United States Patent
Mossman

(10) Patent No.: US 7,781,725 B2
(45) Date of Patent: Aug. 24, 2010

(54) OPTICAL FIBER BASED SENSOR SYSTEM SUITABLE FOR MONITORING REMOTE AQUEOUS INFILTRATION

(76) Inventor: Guy E. Mossman, 270 W. Coleman Blvd., Mt. Pleasant, SC (US) 29464

(*) Notice: Subject to any disclaimer, the term of this patent is extended or adjusted under 35 U.S.C. 154(b) by 252 days.

(21) Appl. No.: 11/822,475

(22) Filed: Jul. 6, 2007

(65) Prior Publication Data

US 2008/0013879 A1     Jan. 17, 2008

Related U.S. Application Data

(63) Continuation of application No. 10/968,975, filed on Oct. 21, 2004, now abandoned.

(51) Int. Cl.
*G01J 4/00*     (2006.01)
(52) U.S. Cl. .................. 250/227.16; 250/227.11; 250/227.14; 250/227.15; 356/32; 356/35.5; 385/54; 385/55; 385/88
(58) Field of Classification Search .......... 250/227.11–227.19; 356/32–35.5; 385/54, 55, 385/88
See application file for complete search history.

(56) References Cited

U.S. PATENT DOCUMENTS

| | | |
|---|---|---|
| 4,634,856 A | 1/1987 | Kirkham |
| 4,866,265 A | 9/1989 | Hohne |
| 5,005,005 A | 4/1991 | Brossia et al. |
| 5,093,569 A | 3/1992 | Krumboltz |
| 5,165,283 A | 11/1992 | Kurtz et al. |
| 5,181,423 A | 1/1993 | Phillips et al. |
| 5,187,475 A | 2/1993 | Wagener et al. |
| 5,196,845 A | 3/1993 | Myatt |
| 5,258,930 A | 11/1993 | Fukuyoshi et al. |
| 5,278,442 A | 1/1994 | Prinz et al. |
| 5,389,411 A | 2/1995 | Cohen |
| 5,515,041 A | 5/1996 | Spillman et al. |
| 5,627,934 A | 5/1997 | Muhs |
| 5,723,857 A | 3/1998 | Underwood |
| 5,995,686 A | 11/1999 | Hamburger et al. |
| 6,080,982 A | 6/2000 | Cohen |
| 6,101,884 A | 8/2000 | Haake |
| 6,466,323 B1 | 10/2002 | Anderson et al. |
| 6,710,328 B1 * | 3/2004 | Mastro et al. .......... 250/227.14 |
| 6,836,326 B2 | 12/2004 | Hajduk |
| 6,981,423 B1 * | 1/2006 | Discenzo ................. 73/800 |
| 2003/0191564 A1 | 10/2003 | Haugse |

* cited by examiner

*Primary Examiner*—Georgia Y Epps
*Assistant Examiner*—Kevin Wyatt
(74) *Attorney, Agent, or Firm*—Merek, Blackmon & Voorhees, LLC

(57) ABSTRACT

Methods and apparatus for predicting service life of remote equipment for infiltration of liquid are disclosed. Such methods and apparatus preferably include at least one fiber optic sensor assembly adapted to react after being exposed to a predetermined quantity of liquid.

5 Claims, 14 Drawing Sheets

Preferred Embodiment for Functional Installation of Fiber Based Humidity and Corrosion Sensor System FIG. 1 Preferred Embodiment for Surface Ship Propulsion Shaft Health Monitoring Sensor System Invention FIG. 2 Preferred Embodiment for Submarine Propulsion Shaft Health Monitoring Sensor System Invention FIG. 3 Typical Propulsion Shaft Application Diagram FIG. 4 Preferred Embodiment for Functional Installation of Fiber Based Humidity and Corrosion Sensor System FIG. 5 Preferred Embodiment for Propulsion Shaft Sensor Layup Diagram FIG. 6 Cross Section View of Preferred Embodiment of FRP Layup Showing Encapsulated Humidity and Corrosion Sensor System FIG. 7 Chart Relationship of Shroud Expansion to Strain (prior art)

FIG. 8 Preferred Embodiment of Humidity/Chemical Sensor Functional Structure (prior art)

FIG. 9 Preferred Embodiment for Corrosion Sensor Based on Strain Acting on a Biconical Fiber Taper FIG. 10 Cross Section View of Preferred Embodiment of FRP Layup on Propulsion Shaft Showing Encapsulated Humidity Sensor Mounted in FRP Half Round Channel FIG. 11 View of Preferred Embodiment of FRP Lay-up on Propulsion Shaft Showing Single and Dual Port Ferrule Structures Fixed to the Shaft or FRP Lay-up with Adhesive.

Submarine Hull Tile Bond Integrity Monitoring Application

Shuttle Protective Tile Integrity Monitoring Application

OPTICAL FIBER BASED SENSOR SYSTEM SUITABLE FOR MONITORING REMOTE AQUEOUS INFILTRATION

This application is a continuation of U.S. patent application Ser. No. 10/968,975 filed Oct. 21, 2004 now abandoned.

BACKGROUND OF THE INVENTION

1. Field of the Invention

The present invention relates generally to monitoring systems employing optical fibers and more particularly to those involving the monitoring of aqueous infiltration.

2. Description of Related Art

The monitoring of corrosion effects on mechanical equipment when operating in a sub-sea or harsh environment is a necessity in many situations. For example such monitoring includes (i) in-situ monitoring the health of aerospace, civil and marine structures for structural deformation effects and the effects of corrosion and water or chemical infiltration into structural material systems including Fiber Reinforced Plastic (FRP) composite material, (ii) monitoring of the long term health of aging aircraft fuselage structural integrity, (iii) monitoring pressure on composite FRP structures which include mast and spar flexing, sail pneumatic pressure and hull deformation and moisture or chemical infiltration or change in any composite material structure.

The following references U.S. Pat. No. 5,258,930 November, 1993 Fukuyoshi et al: U.S. Pat. No. 5,389,411 February, 1995 Cohen: U.S. Pat. No. 6,080,982 June, 2000 Cohen: U.S. Pat. No. 5,165,283 November, 1992 Kurtz et al: U.S. Pat. No. 5,181,423 January, 1993 Phillips et al: U.S. Pat. No. 5,187,475 February, 1993 Wagener et al: U.S. Pat. No. 5,196,845 March, 1993 Myatt: U.S. Pat. No. 5,278,442 January, 1994 Prinz et al: U.S. Pat. No. 5,515,041 May, 1996 Spillman et al. Other references: A. Martin, "A Novel Optical Fiber-Based Strain Sensor", IEEE Photonics Technology Letters Vol. 9 No. 7, July 1997: D. C. Inder, "Evaluation of a low-cost fiber-based strain sensor", SPIE Vol. 3670.0277-789X/99, March 1999: o. Suzuki, "POF-Type Optic Humidity Sensor and Its Application", IEEE 0-7803-7289-1/02: K. Broadwater, "Experimental and Numerical Studies In the Evaluation of Epoxy-Cured Fiber Optic Connectors", 2000 Electronic Components and Technology Conference, September 2000: J. Mrotek, "Diffusion of Moisture Trough Optical Fiber Coatings", IEEE, JNL 0733-8724/01, July, 2001: K. Cooper, "Optical Fiber-Based Corrosion Sensor Systems for Health Monitoring of Aging Aircraft", IEEE, 07803-7094-5/01, May 2001: B. Degamber, "Remote Process Monitoring Using Optical Fibre Sensors", IEEE, 0-7803-7454-1/02, January 2002: N. Yonemoto "Multi-functional Sensing for High-sensitivity Detection of Initial State of Iron Rust", IEEE Instrument and Measurement Technology Conference, May 1988: Y. Chuah, "Wireless Telemetry System for Strain Measurement", IEEE, 0-7803-5957-7/00, July 2000: Royal Navy Procedure UK-DEF STAN 02-304 Part 4/Issue 2 (Apr. 1, 2000) describe related applications.

In addition, the following US Patents describe other related applications, U.S. Pat. No. 5,995,686 to Hamburger et al., U.S. Pat. No. 6,466,323 to Anderson et al., U.S. Pat. No. 5,005,005 to Brossia et al., U.S. Pat. No. 4,634,856 to Kirkham, and U.S. Pat. No. 4,866,265 to Hohne.

There is a particular problem associated with underwater apparatus including docks, ships, barges and other equipment associated therewith as one must generally assume a certain "shelf/operational life" for various instrumentation and or components in order to prevent the apparatus shutting down or encroaching on design limits due to damage from water or other seepage. For example, in the case of some navy ship propulsion shafts, such shafts are automatically taken out of service or limited in operational service after approximately 7 years in use. Sometime the infiltration is close to damaging the components and sometimes it isn't. However, to be sure, to date, the only option is to take the equipment out of service. This is an expensive and often unnecessary waste of time if there has been no damage or no initiation of corrosion.

An easier method to monitor such applications and remote equipment would be highly desired but has not heretofore been developed.

SUMMARY OF THE INVENTION

The present invention relates to sensing infiltration of water or other liquid suitable for use in applications that are remote or not readily accessible, for example, in underwater locations such as underwater propulsion shafts. In accordance with the present invention, there is provided a system of monitoring remote or even underwater equipment using a novel and unique application of optical sensing technology. The present invention provides substantial unexpected benefits to many industries including the shipping and offshore industries.

Additional objects, features and advantages of the invention will be set forth in the description which follows, and in part, will be obvious from the description, or may be learned by practice of the invention. The objects, features and advantages of the invention may be realized and obtained by means of the instrumentalities and combination particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

FIG. 11 includes FRP Lay-up and shows single and dual port ferrule structures fixed to a shaft or FRP Lay-up with an adhesive according to one embodiment described herein.

DETAILED DESCRIPTION OF A PREFERRED EMBODIMENT

Figure 1:
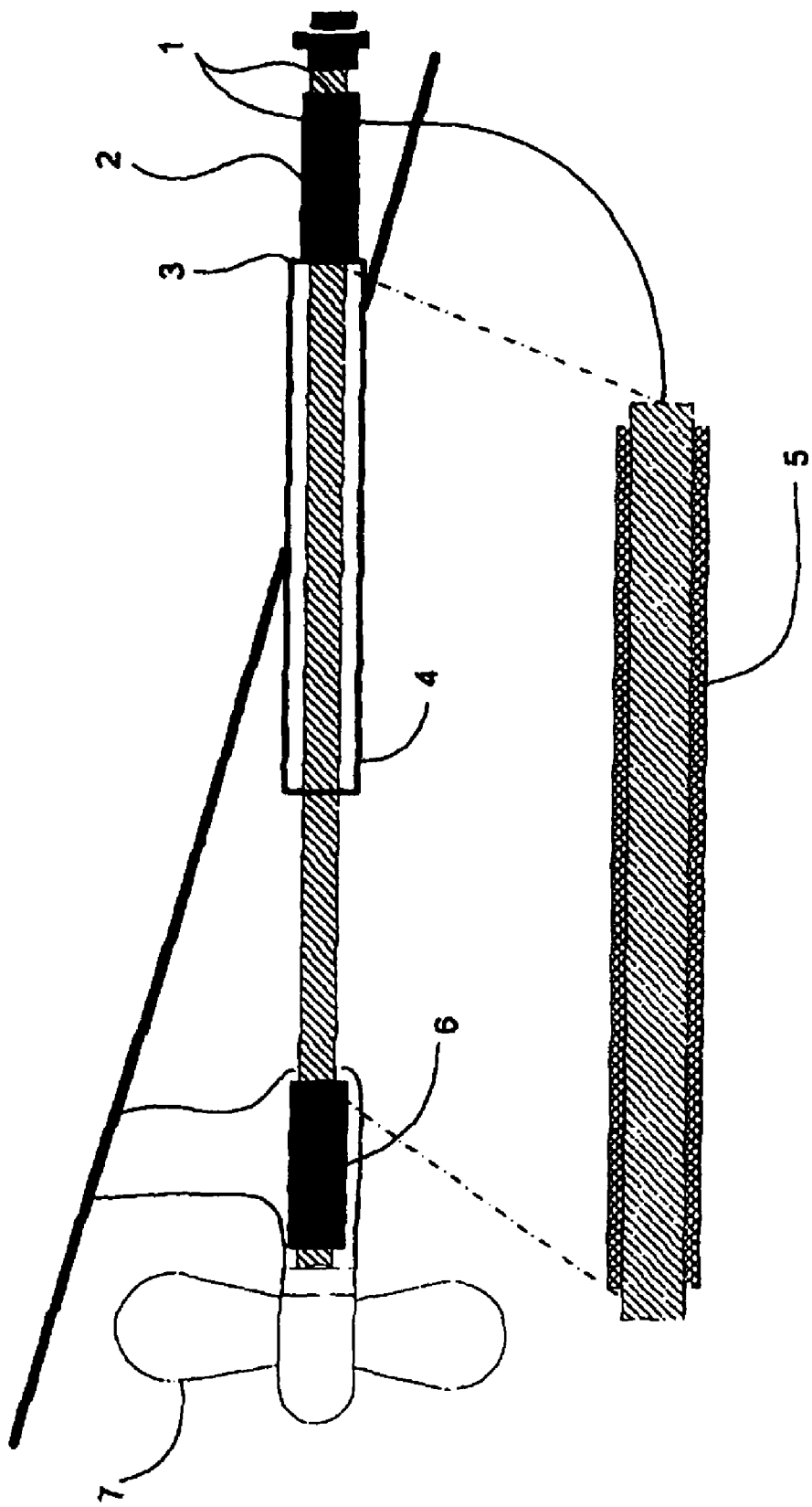
FIG. 1 is a preferred embodiment useful with a surface ship propulsion shaft. The diagram provides a simplified cross-section view of the surface ship application of an embedded optical fiber based sensor system.

The present invention is capable of being used in virtually any application such as the following: (i) in-situ monitoring the health of aerospace, civil and marine structures for structural deformation effects and the effects of corrosion and water or chemical infiltration into structural material systems including Fiber Reinforced Plastic (FRP) composite material, (ii) monitoring of the long term health of aging aircraft fuselage structural integrity, in particular, for example, monitoring the integrity of a fuselage such as an aircraft or spaceship or space shuttle such that one or more fiber optic sensor(s) positioned therein would be capable of reporting any potential or actual damage, however small, to one or more locations so that appropriate remedial measures can be taken to minimize the risks (iii) monitoring pressure on composite FRP structures which include mast and spar flexing, sail pneumatic pressure and hull deformation and moisture or chemical infiltration or change in any composite material structure. The present invention is also capable of being used for monitoring of mechanical seal failure such as for electrical fittings, plugs and adapters as well as virtually any monitoring application where moisture or corrosion might be present.

The present invention provides a system whereby a fiber optic sensor assembly is adapted to predict service life or failure of equipment based on infiltration of moisture and/or strain due to corrosion build-up.

Service requirements for both military and commercial vessels require the fleet to maximize service operation and minimize dry-dock down time. These service requirements are needed to make the most economical use of ship assets through twenty four hour seven day week operation. The embedded optical fiber based sensor system disclosed here will eliminate premature service overhaul and delay occurrence of dry-dock down time. Less down time therefore, less lost duty time thereby reducing expenses associated with dry-dock and needless or accelerated overhaul activities. Adoption and incorporation of the described invention into the lay-up of the FRP cover (shroud) of propulsion shafts, will reduce the over all cost of ownership. The in-situ interrogation of submerged propulsion shafts has a clear benefit of reducing maintenance and support costs by allowing condition based maintenance. Examination of the condition of the shaft with respect to known failure mechanisms due to corrosion while under water has not been successfully achieved due to the complex and harsh environmental conditions. Several new technologies have allowed the realization of the invention described here. The benefits of the in-situ, underwater interrogation of propulsion shafts is manifest in a change in the ship owners maintenance methods. Thus the invention contained herein allows a window of observation in a unique application that heretofore was not possible. Major cost savings occur for the ship industry when condition based maintenance approach is enabled which allows maintenance to take place as needed based on the condition of the propulsion shaft. In contrast to time based maintenance where maintenance is scheduled at fixed time intervals irrespective of the actual condition of the propulsion shaft. Surface ship and submarine currently in Naval service are on a time based maintenance schedule at a cost exceeding $1 M dollars per event taking into account dry-dock costs. After costly removal is performed in dry-dock, at the shipyard, many shafts are inspected and are found to be adequate for continued service. These shafts are removed anyway and replaced with shafts with fresh corrosion protection FRP shroud covering. Incorporating the novel system for inspecting these shafts and parts in-situ and submerged provides useful material performance information and an opportunity to reduce maintenance cost significantly. The novel invention described here will offer the potential for longer service life and reduced total ownership cost for users of remote equipment that can become damaged by infiltration of water, for example, ship owners.

In addition, the present invention is in no way limited to use only with propulsion shafts or marine vessels but also could be readily adapted to a variety of aerospace, civil and marine mechanical structures. Such devices can be fitted with sensors, such as strain sensors, used for measuring various forces or other physical effects to which a monitored structure is subjected. For example, a number of steel and concrete structures, such as buildings, bridges, culverts, and tunnel linings, often include embedded strain sensors. In addition, while a variety of composite structures already incorporate strain sensors, the number of composite structures that include sensors is expected to increase dramatically as composite structures are increasingly utilized in the aerospace, civil, marine and transportation industries.

As known to those skilled in the art of fabrication of composite structures, fabrication generally subjects the composite structure to relatively high temperatures, relatively large pressures and some corrosive byproducts of the catalytic reaction occurring during the curing process. In this invention optical sensors are preferably used in conjunction with composite structures since optical sensors are typically not affected by undesirable effects of curing nor are they vulnerable to the challenges of using electrically powered sensors in a high conductivity environment such as underwater. They can also be used to sense strain and other physical phenomena acting upon the composite structures during the fabrication process. Following fabrication, sensors can be used, for example, to monitor strain and other physical phenomena imparted to the composite structures during service. It is unique and novel to include sensors in such remote applications including for example offshore or sub-sea propulsion shaft anti-corrosive coatings, as a predictor of service life during normal conditions and as a predictor of material fatigue or premature failure during extreme conditions that meet or exceed the original design parameters of the specific composite coatings used to protect sub-sea propulsion shafts from the corrosive effects of the marine environment.

The present invention relates generally to designing propulsion shaft corrosion protection FRP coverings to accommodate monitoring sensors that are embedded or otherwise associated therewith as well as related methods for fabricating such corrosion protection structures.

According to the present invention, a design and preferred embodiment is presented which includes FRP composite structures forming a shroud assembly associated with the lay-up of the anti-corrosion protective coating used to protect underwater propulsion shafts. However, sensors of any type could be provided on any remote equipment that could become damaged or otherwise impacted by undesired infiltration of liquid. By being embedded therein directly or within such a structure such as a compatible FRP composite tube or channel, the embodiment of the sensor system becomes integrated within the device itself, for example, an anti-corrosive barrier coating on a propulsion shaft.

Any suitable sensor can be utilized in the present invention. For example, the sensor described in U.S. Pat. No. 5,995,686 to Hamburger et al. would be suitable and the content of the Hamburger et al. is incorporated herein by reference in its entirety. Alternatively, the sensors of Anderson et al. (U.S. Pat. No. 6,466,323) or Hohne (U.S. Pat. No. 4,866,265) or Brossia et al. (U.S. Pat. No. 5,005,005), the contents of which are hereby incorporated by reference, could also be utilized if desired.

According to one advantageous embodiment, an anti-corrosive barrier coating assembly includes a fiber optic sensor having an element with predetermined dimensions and/or chemical sensing capability, that is embedded within the anti-corrosive barrier coating spliced to an optical fiber having an end portion that extends to the termination on a electro-optical device or a termination connector. By embedding the FRP tubes and/or channels in combination with the sensor assembly of this embodiment within a device that will be used in a remote location, such as an anti-corrosive barrier coating, the fiber optic sensor preferably is adapted to measure a parameter that is dependent upon the conditions, such as the strain, presence of chemical compounds or temperature, to which at least a portion of the structural element is subjected in a manner which averages the measurements over the predetermined dimensions of the sensor element.

Below is described a particular embodiment relating to an underwater propulsion shaft and the below description is not intended as being limited and a similar device could easily be employed on any remote equipment. Nor is the sensor itself limited to the one described but any fiber optic or similar sensor could be utilized if desired for any reason including those mentioned supra.

The FRP composite anti-corrosion coating has predetermined dimensions that are greater than the predetermined dimensions of the sensor element such that the integrated sensing assembly measures the parameter in a manner which can produce spot measurements or average the measurement over a distance that is between the respective predetermined dimensions of the propulsion shaft FRP coating and the sensor element. For example, the propulsion shaft FRP coating will expand due to the buildup of corrosion on the surface of the metallic shaft, causing an increase in the circumference of the FRP coating. By including a fiber optic strain sensor, the change can be measured accurately. As such, the exemplary embodiment measures the strain to which a portion of the structural element is subjected in a manner which can be localized or average the strain measurement over a distance that is irrespective of the length of the sensor element.

Likewise in this embodiment of the invention the FRP composite anti-corrosive coating is under-laid with sensor elements that sense the presence of humidity or liquid water. Thus providing an indication of the presence of infiltration of corrosive electrolytes or damaging molecules between the anti-corrosive coating and the metallic or composite propulsion shaft. This condition would be interpreted as a seal breach in this embodiment.

Accordingly, the FRP encapsulated corrosion sensing apparatus of the present invention both protects embedded sensors such that the fiber optic sensor is embedded within a structural element and thereafter the installed sensor system performs both as monitor and protective coating for the shaft. In addition, the composite FRP assembly can be designed to have thermal, electrical and mechanical properties that are tailored to match or otherwise conform to the properties of the host material of the structural element on or in which the assembly will be embedded.

The invention described herein applies fiber optic sensor technology where it has not been previously applied. This application of fiber sensor technology is novel and presents a significant advance over techniques that could potentially be used, such as electronic sensors, electronic strain gauges, electronic hydrometers, etc., used in the past to monitor the forces and other conditions to which an associated FRP composite may be subjected. Embedding electronics in the FRP is prone to failure over the long term due the extremely harsh environment of the submerged propulsion shaft health monitoring application. Thus in this case fiber optic sensors allow this invention to avoid the traditional electronic techniques which fail to meet the service life requirements due to the corrosive nature of the environment. (water, salt water, pollution chemicals, etc.)

The novel application of fiber optic sensors proposed here has utilized optical techniques to measure strain and other physical phenomena to which the propulsion shaft anti-corrosive FRP cover structure is subjected. As will be apparent, fiber optic sensors are small and more durable than comparable electronic sensors. In addition, fiber optic sensors are less susceptible to electromagnetic interference, have improved corrosion resistance, reduced cabling requirements, have less physical influence on the overall structure, and generally improved measurement sensitivity.

In the invention described herein, fiber optic sensors are encapsulated in a fiber composite material formed of fiberglass cloth and a two-part epoxy. As part of the encapsulation, the sensor can be disposed within the FRP composite and as part of the lay-up may be placed in a vacuum bag or vacuum mold designed to extract unwanted air and excess resin. As such, the resulting embodiment of the encapsulated sensor or array of sensors will solidify in the desired configuration based on custom needs of the specific propulsion shaft configuration.

The proposed embodiment demonstrates techniques and practice required to fabricate and install sensors on the propulsion shaft and are presented herein are exemplary. The practice of FRP lay-up, sensor anchoring, location of the sensor on a propulsion shaft, along with the type of sensor and procedure for interrogation, make up key elements of practical implementation of the invention. Reduced cost of ownership results from using this invention to monitor the health of the shaft while the propulsion shaft is submerged and installed on the host vessel.

Fiber optic sensor attachment to a metallic or composite propulsion shaft requires a number of unique installation techniques. Attachment techniques are representative of one approach but are not limited to those described as the preferred embodiment.

Their small size makes fiber optic sensors relatively difficult to handle. The preferred embodiment represents an attachment method to secure the relatively small sensors and is advantageous in many respects. In addition, fiber optic sensors provide an extremely localized measurement. Placement of sensors requires specific anchoring techniques based on the parameter one wishes to measure such as a localized strain measurement vs. an average strain measurement. The preferred embodiment of the invention provides insight into the condition of the underlying shaft, with regard to corrosion and/or water infiltration penetrating the anti-corrosive FRP cover.

The health monitoring of propulsion shafts by analysis of changes in structural state or chemical make-up of the anti-corrosive cover and shaft mechanical system through periodic measurement of the embedded optical sensor system realizes the claim that the condition of the shaft can be determined in-situ (without removing the shaft from the vessel). These measurements can then be averaged over a long period of time period and over a larger surface area. Long term data collected from periodic sensor interrogation can then be correlated and interpreted.

Fiber optic sensors are quite delicate. As such, the process for fabricating an anti-corrosive FRP cover for protection of the shaft, which must be compliant with military specifications and sub-sea environment, requires the embodiment of the design and process or practice of building a FRP structure to be precisely and reputably accomplished such that uniform service results can be obtained. Fabrication includes the subsequent process of layering the FRP shroud on a propulsion shaft without damage to the embedded fiber optic sensors and with access to the ingress and egress optical ports for termination of the optical circuits to either embedded telemetry circuits or wet-mate optical connectors. As discussed previously the embodiment described herein has chosen, but is not limited to, wet-mate optical connectors.

The invention of the propulsion shaft health monitor and novel practice disclosed herein presents the preferred embodiment of fiber optic sensor attachment to a propulsion shaft through the use of anchor point ferules and pre-formed channel structures in accordance with the invention application and the choice of sensor elements presented herein. The channels and ferrules are made of FRP compatible materials and are thus bonded to the fiber reinforced plastic coating, metallic shaft or composite shaft, thus becoming an integrated sensing system of predetermined topology and sensing capability. Thereafter, the fused structure becomes a permanent attachment to the shaft. As such, the fiber optic sensor is protected by the pre-formed channel or tube from indelicate handling and forces present during the shaft anti-corrosive barrier fabrication and installation processes that could otherwise be destructive.

To average the strain over the sensor length a pre-formed tube or channel generally allows the fiber to stretch. A channel also allows water or chemical infiltrate to pass along the fiber with relative ease. This practice also relieves the fiber from adhesion to the RFP substrate when the application benefits from free movement.

Likewise other sensor applications benefit when the fiber is cast into the FRP lay-up as an integral component glass element. This embodiment provides more localized measurements where sensors are wetted with resin and pressed into the composite material during lay-up, thus forming a solid integrated structure.

In yet another optical sensor configuration the fiber is held in a pre-formed channel against the metallic or composite propulsion shaft whereby the pre-formed channel protects the fiber sensor from the FRP lay-up material leaving the sensor completely isolated and able to sense the presence of chemical agents or corrosive byproducts.

The coefficients of thermal expansion of the pre-formed channel or tube and the host material are chosen to be close to the same or exactly the same. This approach avoids issues known to cause adverse effects suck as material delamination of the pre-formed channel. Additionally, fabricating pre-formed channel structures in identical compatible composite FRP material provides the same susceptibility to corrosion and water or electrolyte infiltration when used for marine sub-sea monitoring.

As such, it is desirable to be able to reliably embed and securely bond sensors, including fiber optic sensors, within a variety of FRP shapes such that the sensors are compatible with the materials currently in use. In this embodiment, it is desirable to provide a fiber optic sensor dressing and routing technique that eases handling and is repeatable and thus less prone to error.

Current techniques for health monitoring are unwieldy and/or inaccurate. The corrosion area of interest may be so situated as to be inaccessible or not readily accessible. Under normal conditions (i.e., when a ship is in the water), it may be an awkward and clumsy proposition for a person to operate a gauge instrument or do a visual inspection at a given location or within a given configuration. In situations involving ship propulsion, it usually requires inspection only during static conditions (i.e., when the ship is in dry dock rather than at sea), the resultant measurements may not be accurate unless the protective anti-corrosive coating is completely removed.

In marine military applications, for instance, corrosion of the main propulsion shaft can result in mechanical failure. Conventional approaches to determining such corrosion have involved manual visual inspection. Lack of access to the entire surface area of the shaft exposed to the corrosive effects of sea water limits inspection to dry-dock maintenance. In fact the shaft corrosion problem forces the Navy to dry-dock the fleet on a time based schedule. This maintenance procedure is directly related to the operators inability to visually inspect large potions of the shaft until the shaft is removed from the vessel during dry-dock.

Propulsion Shaft Description—The propulsion shaft for modern shipping typically consists of three main components. The propulsion shaft, stuffing box, and stem tube make up the major operational components that are discussed here in order to identify the use of the invention.

FIG. 1—Propulsion Shaft Diagram displays the typical mechanical design of a propulsion shaft system. The stem tube is part of the design of most if not all ships and leaves the propulsion shaft inaccessible and thus impossible to make visual inspections to determining risk assessment of the extent corrosion and thus the health of the shaft is indeterminate.

The described apparatus is embedded in the FRP covering for the propulsion shaft. As delamination or damage to the corrosion protective covering of the shaft occurs seepage occurs triggering a change of state of the embedded optical sensor technology. Thus an array of sensors picks up the migration of moisture up the shaft. Interrogation of the shaft sensors provides indication that the shaft anti-corrosive seal has deteriorated. As time passes, and subsequent interrogations of the sensor array are performed, migration of moisture axially up the shaft can be tracked. In areas where the moisture has accumulated and corrosion has commenced, swelling of the shroud can be expected as the corrosive byproducts accumulate under the shroud cover. Over time repeated interrogation of the status of the sensor array will provide continued insight into the progression of the corrosive process and allow accumulation of statistical trend information that will lead to prediction of shaft health and allow for condition based maintenance thus avoiding catastrophic failure based on real time shaft condition assessment.

Since the invention is a novel solution to a pressing maintenance need of the military and industry the invention is independent of the specific fiber sensor technology applied to sense the change of state of the FRP anti-corrosion covering. The invention takes advantage of the fact that corrosive by-products are caused by infiltration of water or chemicals to the space between the protective coating and the shaft. The result caused by chemical reaction of these electrolytes and chemicals with the core shaft material produces corrosion between the FRP coating and the shaft. As shown (FIG. 7) the shaft diameter expands as the corrosive by-products build volume under the anti-corrosive covering. The extent of health of the shaft is detected through the use of two methods by this invention. First the detection of corrosive chemicals infiltrating to the shaft core. Secondly, the detection of swelling of the protective coating covering the shaft resulting from the build up of corrosion byproducts.

The present invention will now be described more fully hereinafter with reference to the accompanying drawings, in which a preferred embodiment of the invention is shown. This invention may, however, be embodied in many different forms and should not be construed as limited to the specific embodiments set forth herein; rather, this embodiment is provided so that this disclosure will be thorough and complete and will fully convey the scope of the invention to those skilled in the art. Like numbers refer to like elements throughout.

Figure 2:
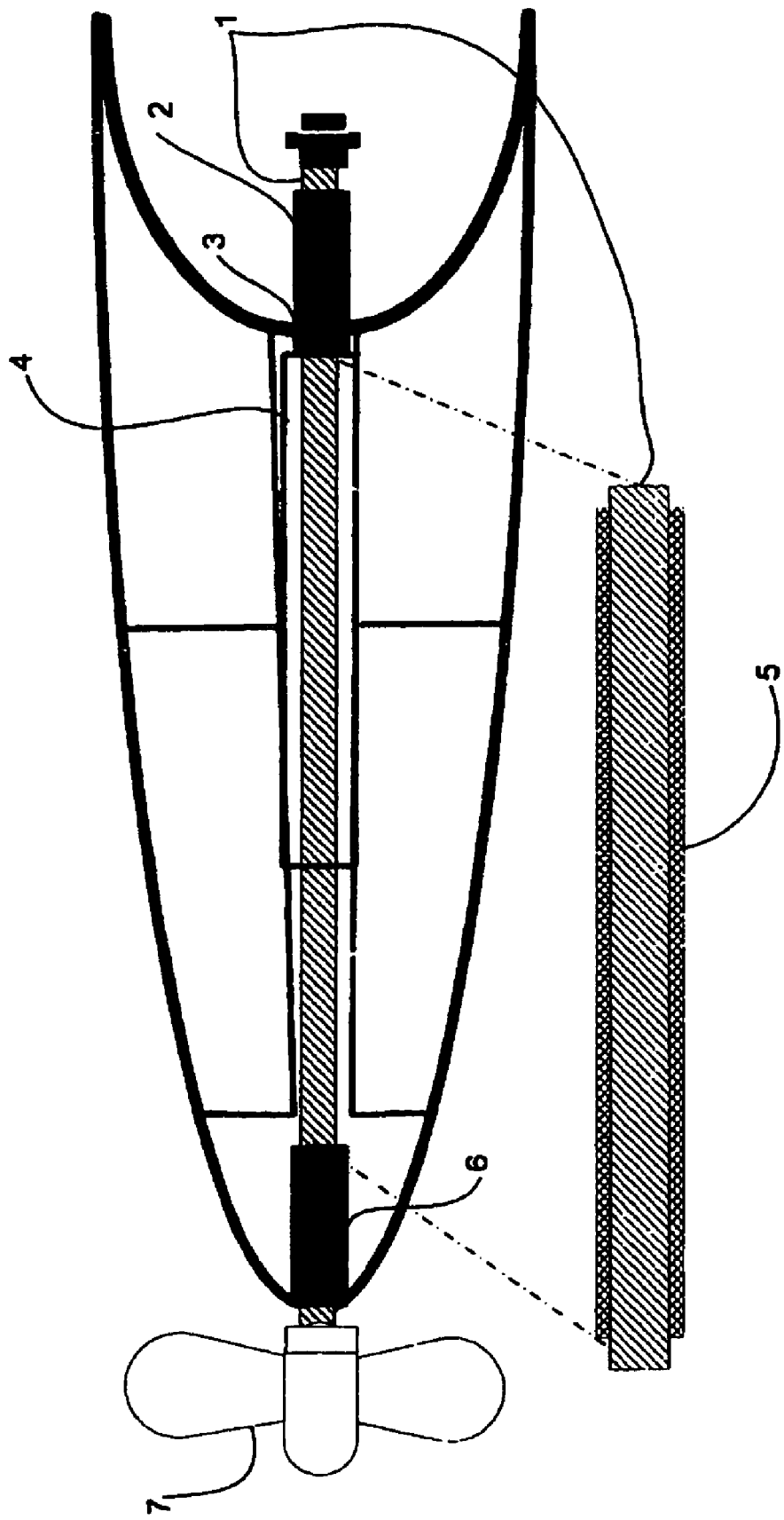
FIG. 2 is another embodiment of the present invention useful for a submarine shaft. The diagram provides a simplified cross-sectional view of the submarine ship application of an embedded optical fiber based sensor system.
Figure 3:
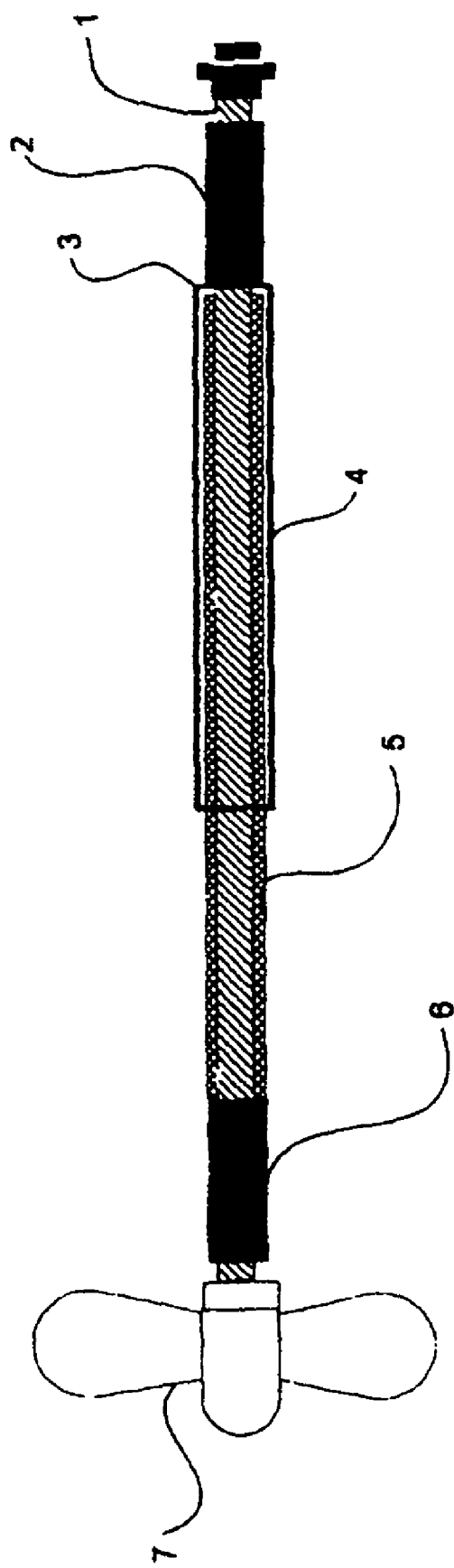
FIG. 3 depicts a suitable propulsion shaft application diagram according to the present invention. The diagram provides a perspective view of a composite FRP corrosion prevention apparatus including an encapsulated sensor according to one advantageous propulsion shaft configuration embodiment of the present invention.

There exists a common problem as shown in FIG. 1 and FIG. 2, and illustrated in FIG. 3. Military commercial shipping and the offshore industry, including submarine applications, have similar needs for anti-corrosion coverings for their propulsion shaft sections that are exposed to harsh sub-sea corrosive environments. This invention provides "real time" monitoring of the health of an equipped propulsion shaft.

Once equipped with the invention, the progression of corrosion and/or shaft degradation can be monitored in-situ and under water without the need to dry-dock or dismantle the vessel for removal of the shaft and visual inspection. It is envisioned that the invention could permit equipment to be checked on a periodic basis such as every 6 months, or every 12 months for example or virtually any predetermined time interval or continuous monitoring.

Provided a ship is equipped with the invention interrogation can be conducted while the ship is in alongside a pier. A maintenance team simply attaches to the sensor array using any type of connector, for example a sub-sea wet-matable connectors or in and alternate embodiment queries an embedded transponder. The sensors can then be interrogated from a test station above water. This concept of providing interrogation and diagnosis of the propulsion shaft condition is novel and unique to this invention and its application to propulsion shafts or military and commercial shipping.

FIGS. 1,2 and 3 show typical propulsion shaft configurations for surface ship, submarine and generic propulsion shaft applications. Elements of the propulsion shaft embodiment to which the invention is to be applied are described as follows: (1) metallic or composite propulsion shaft core; (2) through-hull sleeve bearing through which the shaft protrudes; (3) shaft seal (stuffing box) used to make the shaft through hull watertight; (4) stem tube through which the shaft protrudes towards the final bearing and the propeller; (5) FRP anti-corrosion coating protects the metallic propulsion shaft core from sea water corrosive or damaging effects; (6) final sleeve bearing through which the shaft protrudes; (7) propeller. Since the mechanical characteristics of the composite FRP can be precisely tailored (such as to match those characteristics of the propulsion shaft contours and materials in which the optical sensor system is to be embedded) a secure bond can be formed between the host FRP material and the propulsion shaft material.

Accordingly, the present invention provides a monitoring solution for propulsion shafts. We discuss the invention as it is applied to the preferred embodiment for interrogation of the condition of the shaft core (1) to determine the effects of infiltration of water, chemicals and the resultant corrosive effects. This can be done while the shaft is submerged and without disassembly. As an example of the preferred embodiment we discuss a method for fabricating the embedded propulsion shaft health monitoring sensor system on propulsion shafts on commercial and military ships. Note the shaft configuration. A percentage of the shaft is not inside the ship it is not. The shaft length exposed to the seawater environment is the area where the invention provides a solution for detection of corrosion and/or propulsion shaft deterioration by sensing changes in the state of the FRP corrosion protection coating. It should be noted also that a portion of the external shaft length is encapsulated by a structure known as the "stem tube" making visual inspection impossible.

Figure 4:
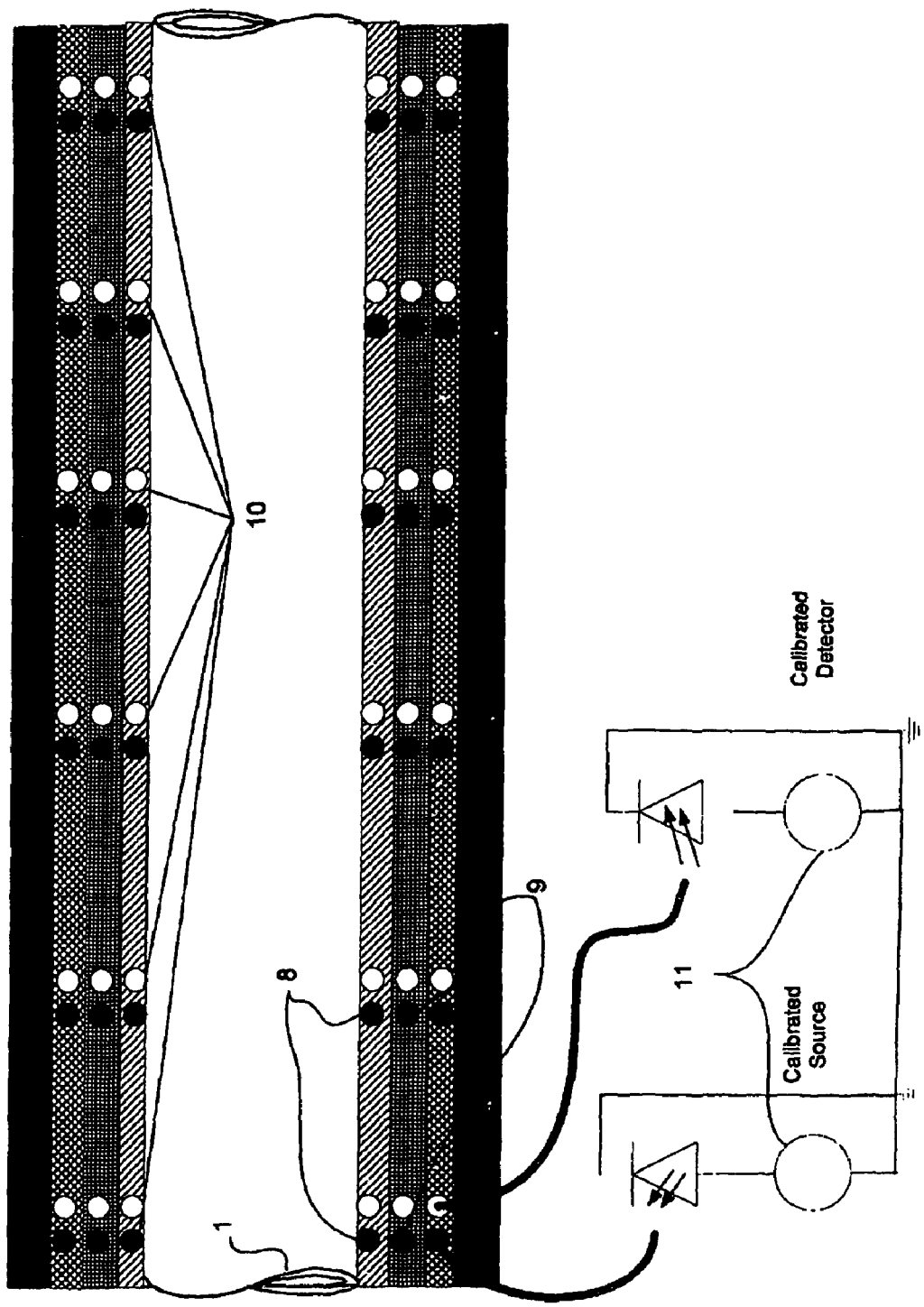
FIG. 4 depicts another embodiment of the present invention relating to a fiber based humidity and corrosion sensor system. This diagram provides a fragmentary perspective view of a propulsion shaft having a composite FRP wrap layered on top of the fiber sensor assembly.
Figure 5:
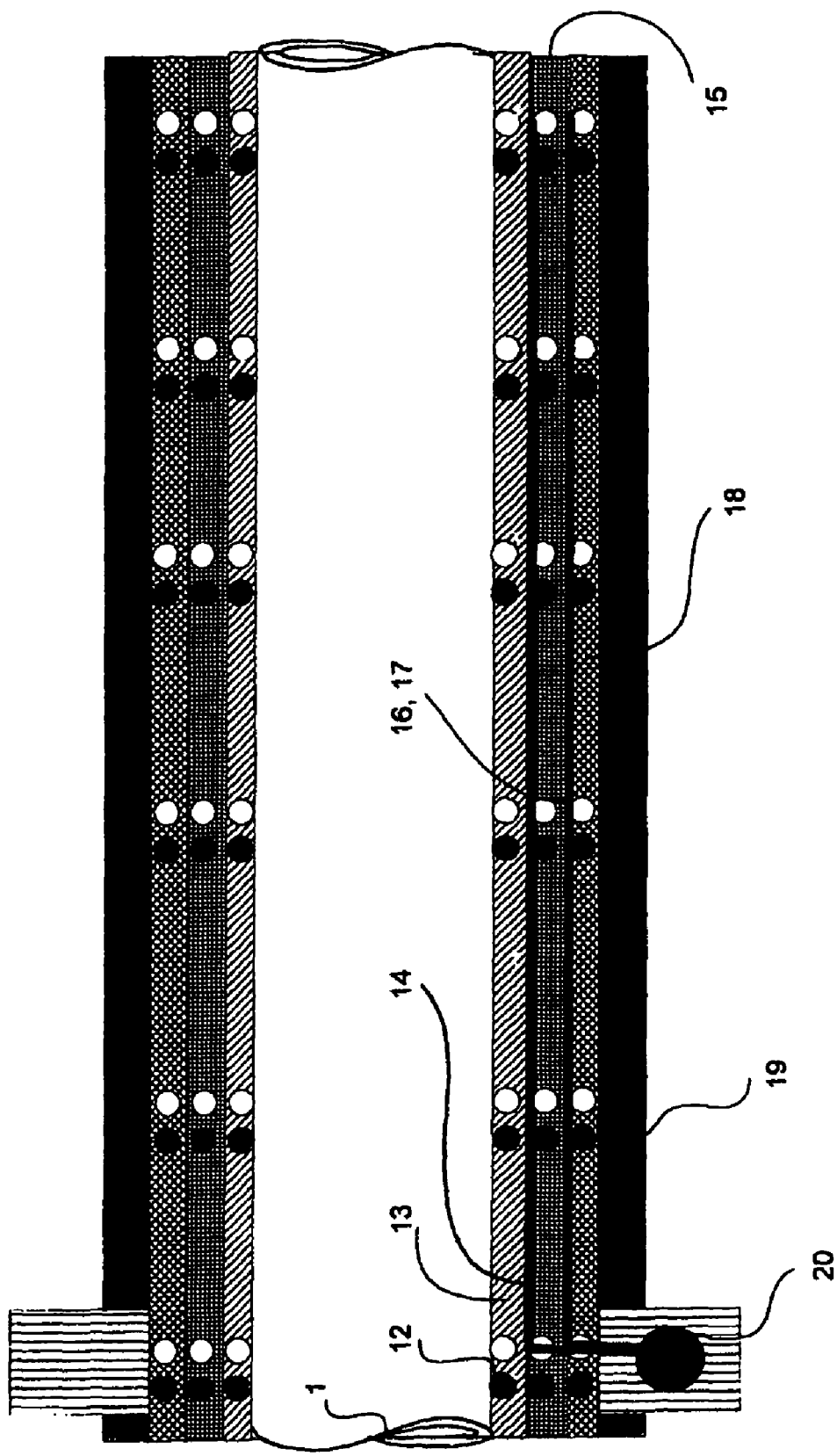
FIG. 5 is a diagram providing a simplified view of lay-up of sensors on a propulsion shaft according to one embodiment of the present invention.
Figure 6:
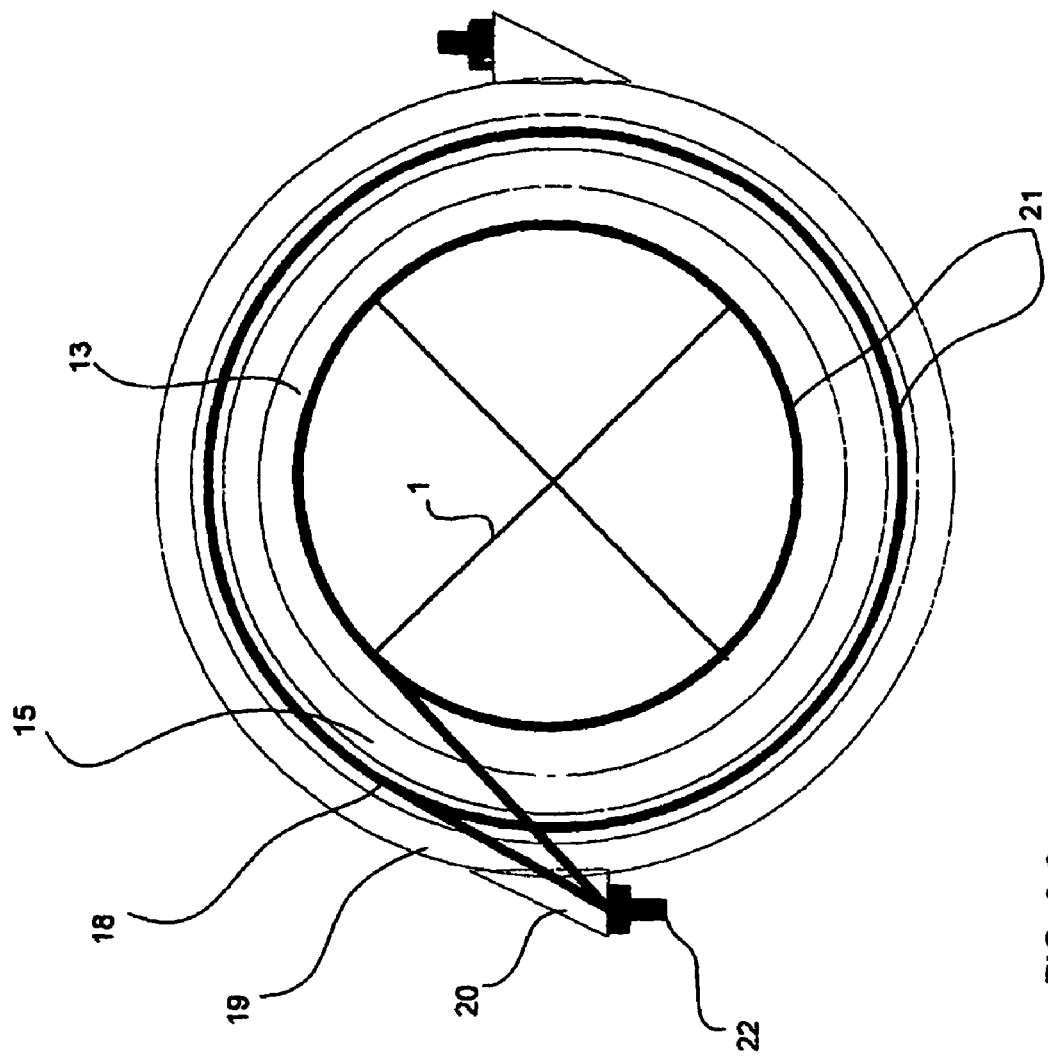
FIG. 6 is a cross sectional view of a FRP Lay-up according to another embodiment of the present invention.

A preferred embodiment of the invention positions a plurality of sensors as shown in FIG. 4. (8), (9), (10) Sensors are preferably located in certain predetermined positions in order to provide consistent results and quantitatively track the condition of the propulsion shaft. As part of this embodiment the sensors can be, if desired, incorporated at the time of anti-corrosion FRP coating installation lay-up. The sensors having an a-shaped lateral cross-sectional and including a plurality of sensors are placed, but not limited to being placed, both under the first layer and under the third layer according to one embodiment of the present invention. In FIG. 5, there is shown an implementation of the invention including optical harnesses used to deliver and retrieve optical signals to and from sensor elements. In this case end attachments are delivered to sub-sea optical connectors in this case or other similar methods to deliver and receive optical signals for telemetric delivery to necessary measurement equipment are not described here. In FIG. 6, a diagram depicts a typical cross section of a propulsion shaft including an embedded humidity and corrosion sensors with ingress/egress optical connection through a "Wet-Mate" fiber connector. Alternative embodiments may include electronic telemetry circuitry and its associated electrical connectors or wireless transponder molded into the FRP on the shaft circumference Ferrule (28) fiber holders are placed according to specific design of sensor types and the routing of the connection fibers. The mat is then laid on top of the sensors, impregnated with resin, and allowed to cure while the fibers remain stationary within the fiber holder ferrules. Thereafter, based on the precise placement of ferrules, routing (30) is consistent and repeatable and the resulting composite FRP assembly can be manufactured repeatedly with consistent sensor results.

The fiber sensors are then baselined using a calibrated optical transmitter source and optical detector forming the final calibrated of the sensor assembly. (11)

A plurality of fiber sensors include a first layer of dry sensor fibers to be used to sense the presence and migration of water or chemicals. (12) The humidity sensors are installed under controlled humidity condition and remain dry or chemical free until such time a breach of seal occurs followed by infiltration. As such, a fiber anchor/holder consisting or ferrules (29), (31) and channels (25) is first disposed about the first layer of the dry fibers is repeated to form a plurality of sensor stations along the shaft (10) and is then encapsulated in Mil-R-23461 or similar FRP cover. Subsequent layers consisting of fiber cloth wetted with resin are then used to encapsulate the first layer and act as a base for mounting interconnect fibers.

After the base layer (13) encapsulating the dry sensor fibers in cured a interconnect is placed above the first layer (14) and is encapsulated in the second layer (15) corrosion sensor are located and secured with ferrules in the third layer. (16) Interconnect fibers for the third layer sensors are dressed to and from each sensor station (10) and encapsulated in layer three. (17) Layer four (19) both encapsulates provides protection for the layer three sensors and allows for molding a support structure for mounting (20) input/output connectors (22). Stations are placed lengthwise (axially) along the shaft forming a plurality of corrosion sensing fibers (10) or a network or array of sensors containing a plurality of humidity (8) and corrosion (9) sensors along the shaft.

The fiber sensor and interconnects are held in place, dressed and anchored using fiber ferules (30). Each layer is routed by design to optimize sensor performance and minimized micro-bend losses. The sensor array consists of a complete four layer coating containing dry chemical/humidity sensors in the first layer (13), encapsulated interconnect fibers in the second and third layers (15) (16), and encapsulated corrosion sensors in layer three. (17) and the third layer (18) encapsulated corrosion sensors and interconnect fibers in the third layer.

Fiber ends of the sensing element interconnect fibers are routed to the position of ingress and egress which is, but not limited to, a wet-mate connector. (22) The light input/output ports (22) are placed in an area (20) accessible to maintenance and safe from mechanical harm. The forth layer (19) is designed to provide both the final coating and the structural substrate to support the wet-mate connector system or an encapsulated electro-optic transducer system (22).

The forth layer (19) provides the protective layer that covers the dressing of the fiber sensor input/output fiber and encapsulation of sub-sea connector field and/or encapsulation of opto-electric transducer, transponder telemetry electronics. These can include telemetry systems such as those proposed and covered under Spillman U.S. Pat. No. 5,515,040 Composite Shaft Monitoring System.

Figure 7:
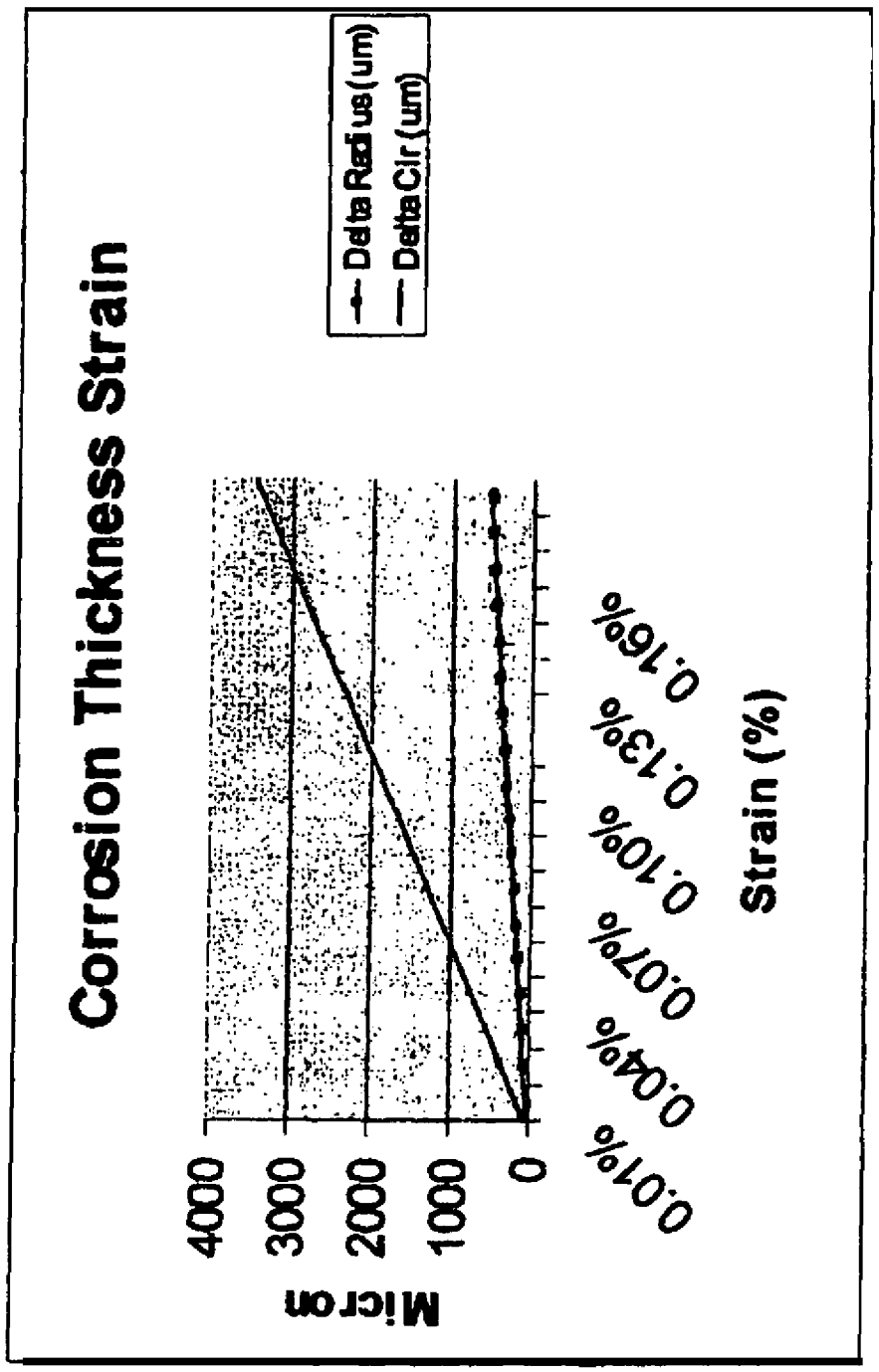
FIG. 7 is a chart showing a relationship of shroud expansion to strain and is a graph that predicts the effective mechanical strain which is then sensed by the embedded optical sensors and results in a detectable change in the transmissive characteristics of the corrosion sensor used in the preferred embodiment when exposed to strain caused by build-up of corrosive material under the protective FRP coating of the propulsion shaft.

In the proposed invention presented here, the inventor has improved and reduced to practice application of optical sensor technology which is unique when applied to sub-sea applications for maritime underwater propulsion shaft health monitoring. The invention is a novel configuration in both concept and design compared with any known propulsion shaft monitoring optical sensor systems. Optical fiber sensors are an attractive approach for making both chemical and physical measurements. Their use to determine the health of a propulsion shaft covered with a FRP coating is unique. As an illustration of the effect of deformation caused by a build up of corrosive byproducts under the FRP cover a chart showing the change in shaft radius and circumference and the induced strain is presented. (FIG. 7)

The embodiment of this application may include input/output connector or opto-electronics encapsulated within the composite assembly. In the preferred embodiment fiber connectors are incorporated into the FRP third layer where the shape of the fiber connector holder can be further shaped or otherwise formed in a predetermined shape (22). As such, FRP assemblies having predetermined shapes, such as predetermined curved shapes, can be readily formed so as to conform to structural elements having various propulsion shaft shapes and sizes.

In this embodiment, the humidity sensing method (FIG. 8) is based on placement of a polymer or glass optically transmissive fiber against the surface of the material part or propulsion shaft. The characteristics the fiber such that in the presence of water the refractive index of the cladding layer changes. The change in index results in a detectable change in the optical characteristics of the fiber. This change of transmissive characteristics could be detected using miniature spectrometry or as a direct loss or signal attenuation event. A series of bandings of the specified fiber under the FRP lay-up as described above will provide station by station indication of humidity and moisture migration under the FRP anti-corrosive cover. Detecting the presence of water or a chemical infiltration is a key indicator as to the initial delamination seal breach of the FRP barrier coating. The indicator represents the initiation of a corrosive breakdown of a metallic shaft. In the case of composite shafts moisture penetration indicates flaws or breakdown of the material structure due to water or chemical infiltration and can be used as a failure prediction indicator.

A second optical sensor method (FIG. 9) is based on placement of a glass optically transmissive fiber in the middle of the FRP barrier coating lay-up. The FRP barrier lay-up is effected by the stresses and strains of the vessel movement as well as the force environmental conditions acting on the FRP surfaces. When used as a protective layer for corrosion prevention for submerged propulsion shafts, a breach of seal resulting in corrosive activity under the FRP coating can be detected. The corrosive activity causes a thickening film to develop on the surface of the propulsion shaft. The thickening film causes expansion of the FRP shroud thus causing strain in the optical fiber sensor embedded within the FRP.

Through the sensing of humidity using the first sensor method to detect the presence of water molecules and employing the second sensor method using the capability to detect hoop strain due to corrosive build up. The condition of the propulsion shaft can be determined. A detailed description of the sensor design and its function as it applies to solving interrogation of an in-situ propulsion shaft is presented below.

Figure 8:
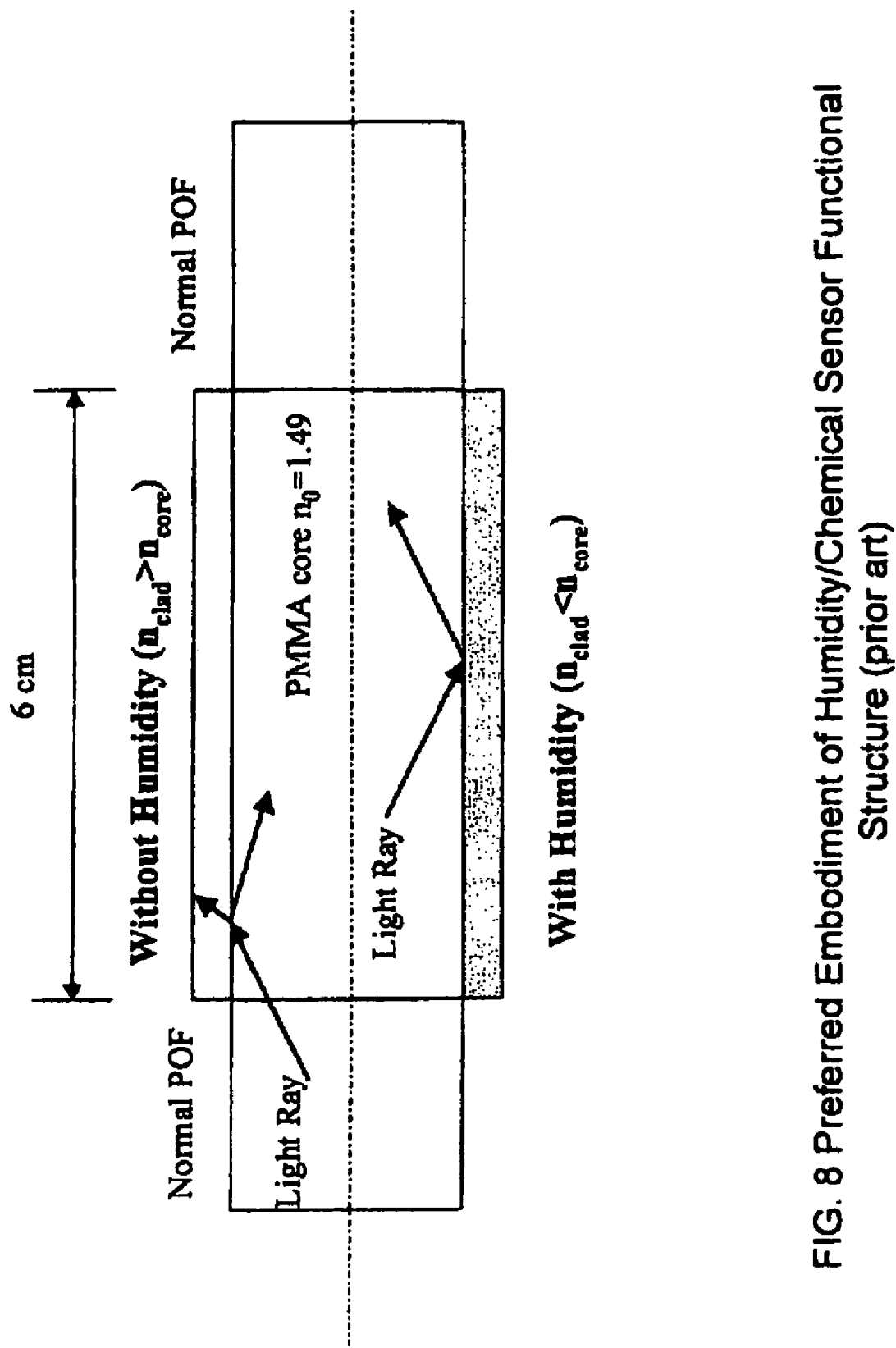
FIG. 8 is a diagram that provides a functional view of a Plastic Optical Fiber (POF) structure according to one embodiment of the present invention that includes a humidity or chemical sensor. In this embodiment the change in the refractive index is, for example, a result of the presence of water molecules and thus drives a change of state of the sensor.

The first sensor method is diagrammed in FIG. 8. In this preferred embodiment of the propulsion shaft sensor used, but not limited to, a sensor technology consisting of Plastic Optical Fiber (POF). Other optical sensor embodiments and materials may be substituted for the preferred embodiment included in the disclosure of invention. Techniques using technology such as Fiber Bragg Gratings (FBG) and machzender interferometer or spectrographic techniques may be substituted as alternative approaches used in place of the POF sensor. The preferred embodiment uses POF for simplicity of sensing and reduced cost associated with using this technology. Different customer requirements and different chemical sensing requirements dictate the preferred sensor solution based on prior art.

As an example: The humidity sensing sensor design used in the preferred embodiment is based on a plastic optical fiber working on the principle of the changing state of the index of refraction between the clad layer and the core of the optical fiber. Simple paF type humidity sensors use a combination of swelling polymers to clad the fiber core. The polymers change state based on the humidity in the environment. The change of state causes a change in the guiding properties of the paF. As the cladding layer absorbs water molecules the index of refraction changes from an index greater than the core to an index less than the core. This change of state is referred to as a structure change from a leaky plastic optical fiber to a guided paF. The technique is sensitive to changes in relative humidity ranging from 10% to 100%. There is a sensitive knee in the curve based on the formula of the polymer clad coating that sharply changes transmissive characteristics when relative humidity reaches between 60-70% and continues through 100%. It is this sharp change in transmissive characteristics that will be used to indicate presence of water migrating between the shaft and the shroud.

The POF sensors are fabricated by coating the core POF with swelling polymers. It is well known that certain kinds of polymers swell when water molecules attach themselves to the polymer. The attachment causes the change in index of the clad layer of the paF and the sensor is triggered. If the cladding layer is set to a higher index of refraction than the core the fiber tends to leak. leaks imply that the rays are not constrained to the core of the fiber by the cladding. Instead there are a certain percentage of photons which escape the core and exit the fiber. However when the fiber is exposed to water vapor the cladding begins to swell through the attachment of water molecules. The index in the cladding begins to decrease and becomes lower than the index of the core. When this happens the paF changes to a guided mode in which the rays of light are completely contained in the core of the fiber and little light energy is lost. The increase in transmitted energy is thus sensed and the sensor has detected the presence of water.

Experimental results done by industry researchers indicate the sensor will be triggered at approximately 60-70% relative humidity. More sensitive sensors than shown in this example can detect smaller concentrations of chemical or humidity at a higher cost. Sensor such as Fiber Bragg Gratings provide for the more sensitive detection at based on the requirements of the customer. The lay-up of the sensor could be as described herein.

Figure 9:
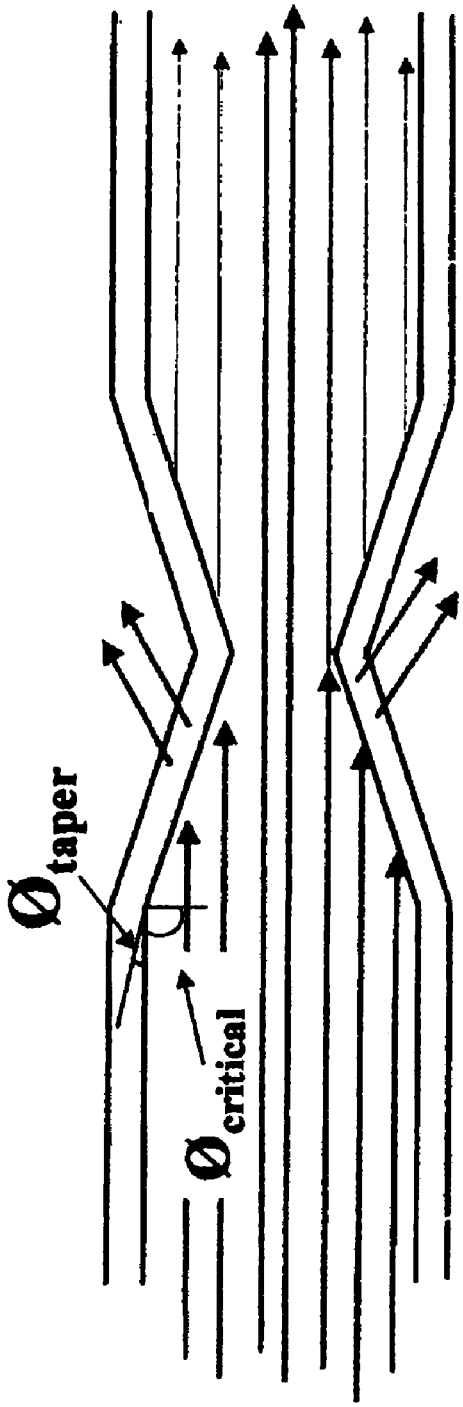
FIG. 9 is a diagram showing a corrosion sensor based on strain acting on a biconical fiber taper according to one embodiment of the present invention. The diagram depicts the functional characteristics of a corrosion sensor based on the effects of strain on the transmissive structure of a biconical taper to trigger changes in state of the corrosion protection FRP layer due to induced strain.
Figure 10:
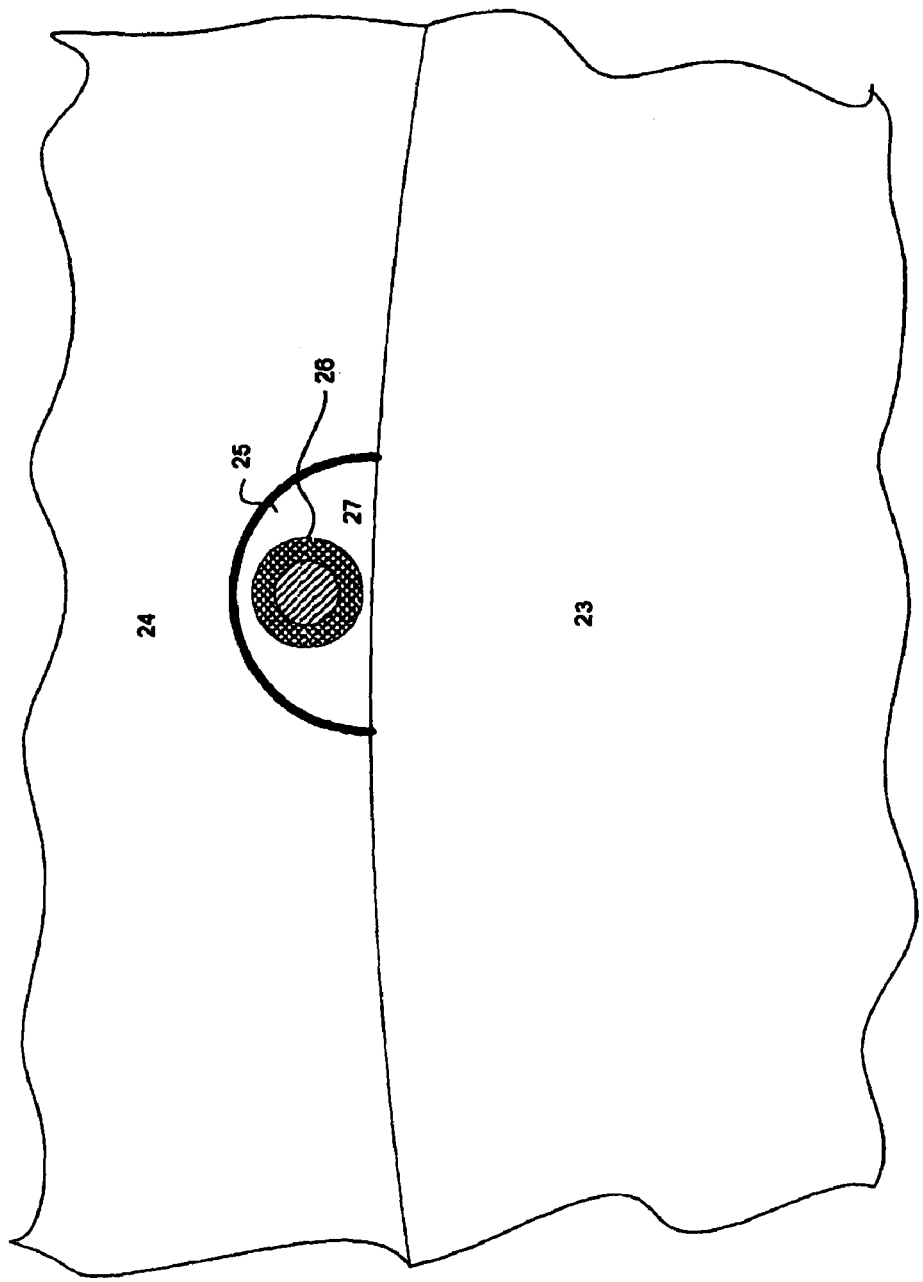
FIG. 10 is a cross sectional view of a FRP Lay-up on a propulsion shaft mounted in a FRP channel according to one embodiment of the present invention. The presence of the channel permits, for example, uniform distribution of strain for the fiber based strain sensor and/or uniform humidity or chemical exposure for the plastic fiber based humidity or chemical sensor.
Figure 11:
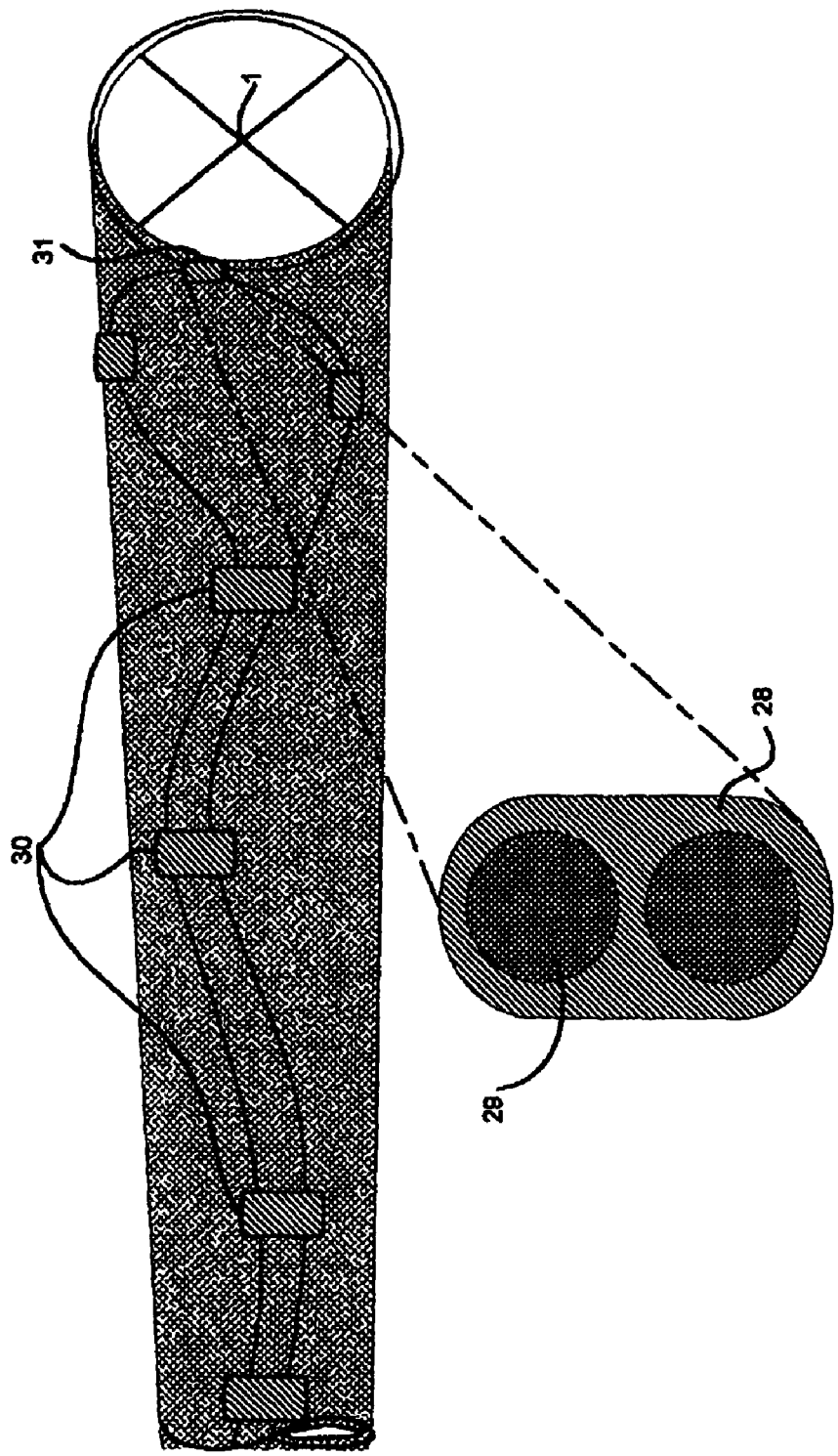
FIG. 11 shows structures that provide routing of connection fibers and tensioning and allow for pre-straining of banded corrosion sensors according to one embodiment of the present invention.

The second corrosion sensing method example is shown in FIG. 9. In this preferred embodiment of the propulsion shaft corrosion sensor, an optical sensor is used to sense hoop strain.

In the description of the preferred embodiment we have chosen, but are not limited to, a biconical multi-mode fiber sensor. Similar sensor may be used in the invention to sense hoop strain. Techniques using fiber sensors such as Fiber Bragg Gratings and mach-zender interferometer as alternative approaches for strain sensing can be used in place of the multi-mode strain sensor presented here.

In the preferred embodiment, the corrosion sensor design is based on the principle that the byproducts of the corrosive process where by water reacts with forged steel produces $FeO_2$ or iron oxide. Iron oxide occupies more volume than the steel and causes the surface area of the corroding surface build up thickness. In the case of a composite shaft the shaft may swell when contaminated with sea water. The build-up in thickness causes the circumference of the propulsion shaft to increase. The added dimension causes the FRP cover to expand which in turn stretches the embedded fiber sensor corrosion sensor causing a strain to be induced in the optical fiber sensor. When the sensor is then interrogated using the same technique described above for the humidity sensor, the results will indicate the increased strain and the presence circumference change and thus the severity of corrosion based on the volumetric changes in dimension of the FRP coating due to build-up of corrosion.

It should be noted that the ratio of expansion of radius to circumference is such that a small build up of corrosion of 30 um will result in an increase in the a 6 fold increase in circumference or 180 um. The 30 um increase represents a 0.01% strain. The expansion in the radial measurement of the shaft and the resulting circumference change is shown in FIG. 7.

The corrosion sensor is a fiber optic device. This approach takes advantage of research into novel intensity based optical fiber strain sensors. In this approach a conventional multi-mode (50j125J.1m) fiber is drawn-down to give a reduced cross sectional area that resembles a symmetrical taper. The sensor will then be embedded into the FRP or fiber reinforce epoxy composite compliant with MIL-R-23461. When subject to strain the "hoop sensor" will cause a change in the transmissive characteristics of the optical fiber. When placed under strain the effected fiber will allow increased optical transmission linearly proportional to the strain acting on the sensor.

Research into the appropriate strain sensor for this novel application indicates a tapered section can be introduced into a length of multi-mode fiber producing the needed results. The sensor is designed such that the taper region effects the Numerical Aperture (NA) of the fiber and thus effects the light transmission. When this tapered region is strained, the geometry of the taper is altered causing a change in the effective NA and therefore a change in the transmission characteristics of the optical fiber.

The tapers can be introduced into the using various methods. Results of experiments have indicated that the response of the sensor becomes more pronounced as the taper angle is increased with respect to the Z axis.

FIG. 9 shows light entering a biconical tapered region. As the tapered section of the fiber deforms due to mechanical strain the biconical effects the passage of light more than the rest of the fiber and thus triggers the sensor. The triggered response is considerably more pronounced when compared with UN-tapered optical fiber. There are three discernible sections of an optical fiber biconical taper: the down taper, the waist and the up-taper as shown in FIG. 9 above. The down taper reduces in radius along the Z axis, or the length of the fiber, until the waist region where it remains constant for a length. The up-taper region expands in radius along the Z axis until the taper returns to the normal fiber dimensions. The propagation of light is altered when it enters the tapered region. The angle of down taper effectively reduces the numerical aperture and light is lost into the cladding due to the change in the angle of incidence of the light rays to the edge of the cladding Theta-Taper vs. the normal angle of incidence Theta-Critical. This variance in incident angle manifests itself in the effect that less light is passed through the waist region of the sensor.

Where m is transmission of the profiles sensor and Theta-Critical and Theta-Taper represent the critical angle and the taper angle for the multi-mode fiber when the sensor is in a strain free condition, Epsilon is the axial strain along the fiber (Z axis) and Gamma is the Poisson ratio.

Conventional 50/1251.1m multi-mode, step index optical fiber with a polyimide coating have been used by researchers to fabricate strain sensors.

The Sensors being fabricated as described herein. The attachment to the propulsion shaft is undertaken using to band the metallic or composite shaft prior to the application of the anti-corrosive FRP coating with humidity or chemical sensors whose characteristics vary from a transmissive or spectrographic prospective in the presence of water or other chemicals and hoop strain sensors to indicate the progression of corrosion e.r .the FRP coating.

The bands are made up of prefabricated single or multiple sensor fibers placed around the circumference of the shaft. The ends of said fibers are threaded through two or more port ferrules and a strain is placed on the fibers to pre-tension them to prescribed strain.

The locking ferules (29), (31) are then attached to the fiber cladding with adhesive material such that uniform placement of fiber sensors can be made at each layer of the fRP composite according to the customer requirements.

Interconnect fibers are routed using ferules attached to the surface of the FRP composite layer on which routing is to occur using adhesive the routing such that the connection is made between said sensors and said optical ingress/egress connector or in-situ opto-electronic circuits used for telemetry therein.

In the preferred embodiment, the sensor will be fabricated and embedded in the shaft coating as described above. Once the sensors have been formed the sensors will be illuminated using a LED which will inject the light into the source end or the sensor. FIG. 4 provides a diagram that indicates the placement of functional humidity detection sensors embedded under the first layer. The fiber sensor having contact with the shaft material and being contained in FRP channels has the capability to change state as water or a chemical infiltrates the shaft. The sensor is lighted with source and the light interconnected to the sensor by an umbilical cable attached from the surface to the shaft via wet-mate connector. The light is then guided through he interconnect fibers to the sensor element. Once the light has passed through the sensor element it is guided by a second interconnect fiber out to the wet-mate connector and through the umbilical cable and is terminated on a sensitive detector. An alternative embodiment would attach the embodiment of the humidity sensor to an embedded telemetry system which would make use of embedded opto-electric light source and detector. Interconnection via a telemetry scheme similar to the Spillman patent referred to above.

In-situ calibration of sensor array using an Optical Transmission Time Domain Reflectometer (OTDR) to baseline the in-situ sensors and measure connector insertion loss.

Connector covers are used to prevent water form sitting on connectors and the connector covers are held in place by a rubber girdle to protect them from shaft rotation turbulence.

Umbilical cables from the surface ship enable technicians or crew to run a series of tests to discover changes in the state of the health of the shaft etc.

In-situ interrogation of the embedded sensor array is embodied in the procedure outlined herein or similar procedural steps designed to isolate and detect the optical transmissive characteristics of the in-situ optical fiber sensors.

Access to the sensors is enabled through the use of waterproof, wet-mate fiber optic connector system chosen for their specific pressure and turbulence characteristics. The said wet-mate connectors are mated producing an optical connection with intrinsic optical loss due to misalignment of fiber ends and refractive index mismatching. The said connector being mated a procedure is then initiated to characterize the connector loss in order to isolate the specific loss of the sensor being interrogated.

An Optical Transmission Time Domain Reflectometer (OTDR) can be used to detect loss in the connector system. The resultant loss of the fiber connectors is then noted and thus removed from the calculation of the transmissive losses of said fiber optic sensor.

Calculations are made of the over all loss of the specific sensor or an array of sensors. The loss and transmissive characteristics of the system are then compared with the initial baseline characteristics recorded on the manufacturing floor while the propulsion shaft existed in a healthy state.

Changes of the transmissive effects are then correlated with both historical and experimental tabular and graphical results. The state of the corrosion and/or chemical or humidity present under the FRP shroud is then presented the customer based on the signature of the specific results obtained therewith.

A series of identical interrogations conducted on all the sensors and sensor arrays embedded in or under the FRP anti-corrosive coating indicate the complete condition of the propulsion shaft. A profile is then prepared using the correlated data and an associated data reduction software package to present integrated results in the form of health report to the captain and/or concerned engineers.

The wet-mate connector system is then disconnected, any protective covers are replace over the sub-sea connectors and the vessel is placed back in service or ordered to dry-dock depending on the results of the integrated propulsion shaft health monitor report.

The invention thus allows for deferral of maintenance until necessary based on the actual condition of the propulsion shaft corrosive condition. The invention allows for a change of maintenance activities from a time based propulsion shaft maintenance approach to a condition based maintenance approach. The result of this change allows for saving for the customer of moneys in the order of millions of dollars per shaft which is significant. Secondly the system offers the customers the possibility of avoiding catastrophic propulsion shaft failure. These failure can cause the vessel to become disabled in a uncontrolled situation and perhaps sink from the collateral damage to the ships systems.

Specialized covers can be used to prevent water from infiltrating connectors. A rubber girdle may be placed over the outside of the connector field in order to secure said connectors from the effects of high speed turbulence brought on by shaft rotation.

Umbilical cable from the surface allows an operator to run tests from above water while the propulsion shaft remains submerged. This configuration allows the operator to run a series of tests at first to discover changes in sensor characteristics such as optical loss and frequency response changes for use in spectrographic analysis of in-situ sensor arrays.

The invention discussed presented will sense and report failure of FRP due to presence of humidity, delamination and subsequent corrosion. The application of sensor systems within the protective coating of underwater propulsion shafts thus providing interrogation and diagnosis of said propulsion shaft in-situ. The application and practice of installation and interrogation of said sensors in order to determine the condition (health) of the propulsion shaft while under water is novel and unique to this invention. FIGS. 1 and 2 are typical of the common elements which are required in most propulsion shaft designs.

According to the present invention, there is provided a fiber optic sensing system apparatus that solves a known commercial issue related to examination of in-situ propulsion shafts, under water, to detect the presence of delamination and corrosion. Delamination of the protective FRP (Fiber Reinforced Plastic) structures underwater can cause seal breakdown and therefore failure of anti-corrosive protection for propulsion shafts thus exposed to harsh corrosive environments. The corrosion detector combination comprising an optical fiber lightguide placed in contact with the propulsion shaft and an optical fiber guide placed in mid composite lay-up, said fiber optic guide including at least one optical fiber, composite material such as that listed below, said fiber optic line accessing and exiting said FRP composite whereby a segment of said fiber optic line is embedded at said propulsion shaft surface and subsequent higher layers whereby:

a mil spec FRP Mil-R-23461, Type 1 or similar composite material, comprised of resin and a fiber glass mat component that is applied in 4 or more layers of impregnated glass mat material thus making up a corrosion protective layer of composite FRP material.

An FRP coating can be applied to propulsion shaft sections that are exposed to the corrosive environmental effects of sea water, water infusion, galvanic action, chemical byproducts of corrosion, environmental pollution and organic water borne organisms. Alternate types of optical corrosion and chemical sensors can be used such as Fiber Bragg Grating based sensors, glass fiber, plastic optical sensors and fibers with organic coating sensors. The invention herein presented claims the novel application of all such optical sensor technologies. Specific sensors have been chosen and presented as the preferred embodiment but the invention is the application of fiber sensors to detect the condition of an underwater propulsion shaft and is not limited to a specific optical sensor technology for fiber based propulsion shaft health monitoring fabrication.

Dimensions and measurement elements are chosen based on the mechanical configuration of the propulsion shaft and the customers requirements for corrosion or chemical infiltration detection.

A fiber optic sensor array of the present invention can be disposed within FRP to thereby form a composite FRP assembly. If desired for any reason, there can be provided a duplication of fiber optic sensors that comprise sensor elements embedded within said composite FRP and optical fiber having an end portion that extends to a termination point external to the FRP coating containing the sensor elements and embedded in FRP layer which provides mechanical stabilization. The system includes a sensor element or many sensor elements having predetermined characteristics adapted to measure a predetermined parameter.

The corrosion detector combination preferably comprises a light emitter and a light receptor, said light emitter connected at a first end of said fiber optic line, said light receptor connected at a second end of said fiber optic line, wherein said shaft surface is in contact with stationary plastic optical fiber, wherein a second glass fiber guide is embedded in FRP layers, wherein said light emitter emits a first amount of light, wherein said light detector receives a second amount of light which follows the transmission of said first amount of light through said segment of said fiber optic line, and wherein the intensity of said second amount of light versus said first amount of light is a function of the deterioration of said segment of said fiber optic line.

The FRP preferably has predetermined dimensions that are greater than the predetermined dimensions of said sensor element such that changes in the composite FRP assembly are reflected in dimensional, chemical or thermal characteristics of the overall assembly and are then measured by the said sensor apparatus indicating a change of state with regard to a predetermined parameter measurement capability of the embedded optical sensor. The sensor fibers can be laid up at various specified radial positions within the FRP determined by the nature of the dimensional, chemical or thermal characteristic to be measured. Further, the sensor fibers can be placed in axial lengths along the propulsion shaft based on the parameter to be measured. In addition the sensor fibers can be placed in circumference on the propulsion shaft prior to the lay-up in order to maintain contact with the metallic or composite shaft material.

The optical fiber sensors are deployed providing light transmissive and optical refractive characteristics which change when exposed to chemicals. (e.g. water, corrosive by products, contaminating chemicals) In some embodiments, the FRP experiences axial strain and thus axial distortion of the original fabricated dimensional design. Axial sensors embedded in the FRP coating will detect said distortion of shape.

A system of the present invention can include a plurality of sensor assemblies associated within said propulsion shaft at a plurality of respective positions, wherein said FRP support an array of sensors that are interconnected by the optical fibers to form a shroud or array. Respective locations of said fiber optic sensors such that the predetermined parameter is measured at the plurality of respective positions at which said sensor assemblies are located.

According to the present invention, there are provided methods for fabricating a composite FRP assembly to incorporate placing sensors comprising the steps of: a) positioning a sensor within the FRP composite fibers that are wet with resin, wherein the sensor comprises a sensor element and a lead that extends outwardly therefrom; b) describing a fiber holder and anchoring practice about at least a portion of the wet FRP fibers such that the sensor input output fibers extend lengthwise through the fiber connector assembly, wherein said disposing step comprises disposing the fiber holder about the portion of the wet fibers within which the sensor element is positioned such that an end portion of the lead extends beyond the fiber holder and is terminated on an assembly of electro-optic driver/detectors or connector array fields; c) describing the use of dual port ferrules to "—anchor the fiber sensor assemblies to the shaft prior and during the lay-up procedure; d) curing the resin while the fibers remain stationary within the fiber holder, ferules and connector assemblies;

and e) placing a protective cover over the exposed connector fields " the resulting in a water tight composite FRP/Sensor assembly.

The method can further include shaping the FRP/Sensor assembly into a predetermined curved shape between said disposing and said curing steps such that the resulting composite FRP/Sensor assembly retains the predetermined curved shape. The fiber holder generally defines a lengthwise extending axis and a lateral cross-sectional shape. The disposing optionally comprises shaping the portion of the FRP and encapsulated wet fibers to have the lateral cross-sectional shape defined by the connector holder or transducer interface.

According to yet another embodiment the lateral cross-sectional shape of the fiber holder/connector assembly is circular, and the shaping step comprises shaping the portion of the wet FRP composite and sensor fibers to have the circular shape defined by the lateral cross-sectional shape of the fiber holder/connector assembly as presented in the propulsion shaft contour.

A fabrication method is provided herein to permanently affix fiber optic sensor elements to propulsion shafts using dual ported ferrules to ensure sensor stability during lay-up. Fabrication methods of the present invention can use tubular channels if desired to isolate, protect and route and optical guide fiber sensor material to the proper location an adhesion as required for specific designs.

Figure 12:
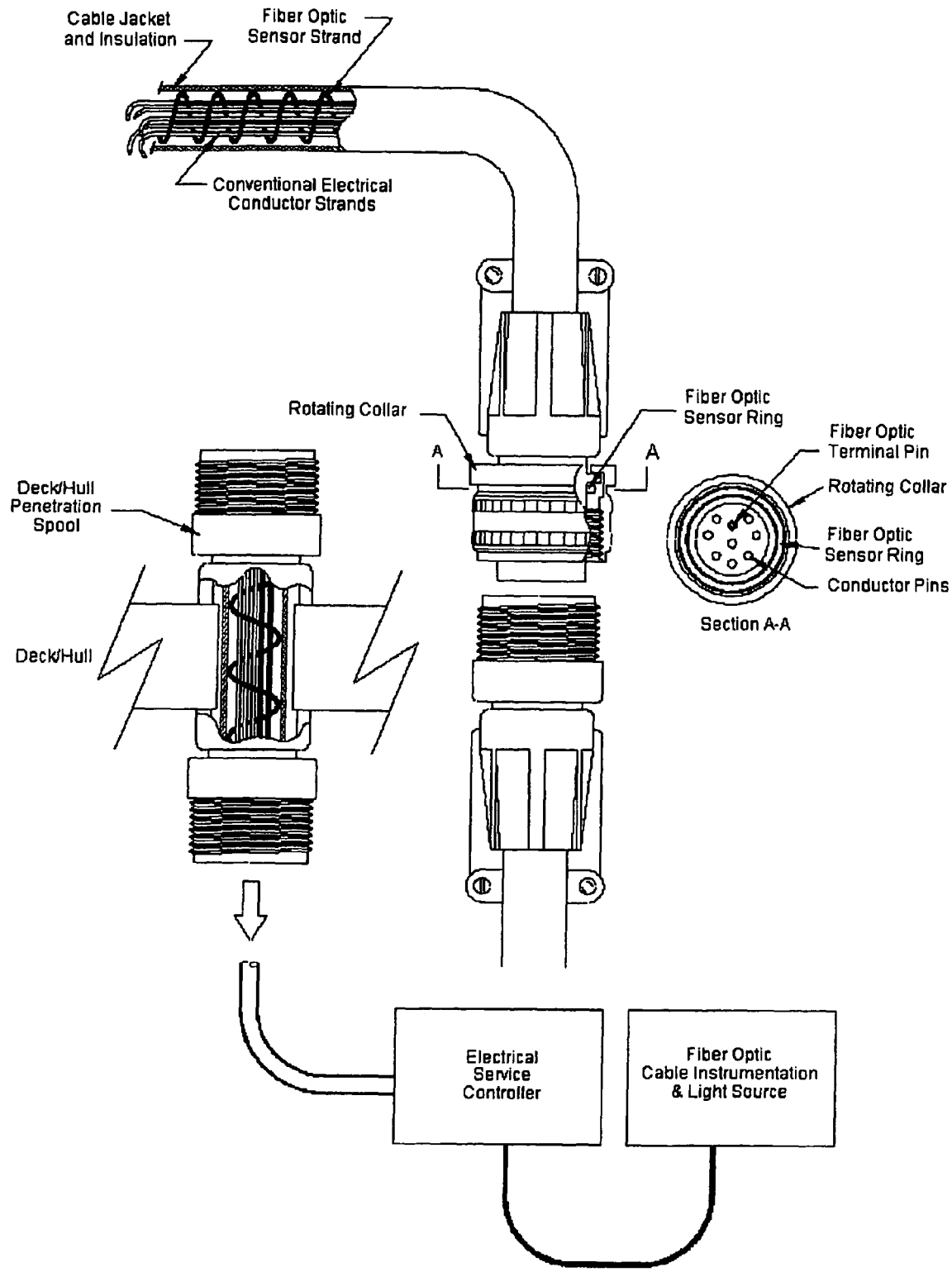
FIG. 12 is another embodiment of the present invention useful for electrical fittings. In this embodiment the change in the refractive index is, for example, a result of the presence of water molecules and thus drives a change of state of the sensor. Also sensing of strain distribution for the fiber based strain sensor and/or uniform humidity or chemical exposure for the plastic fiber based humidity or chemical sensor is an indication of boundry degradation.

A suitable method and apparatus for electric connector monitoring applications is shown in FIG. 12. In FIG. 12, a fiber optic sensor strand is placed within any connector such as an insulated electrical connector. In detail, as shown by the cross section shown as A-A, a fiber optic sensor ring is provided within the electric conductor. A fiber optic terminal pin is provided within the sensor ring and alongside the conductor pins within an insulated jacket of the connector. Fiber optic cable instrumentation and a light source is included whereby information regarding possible breach of the connector is facilitated. Such breach includes information regarding presence of water, corrosion, delamination, and the like.

Figure 13:
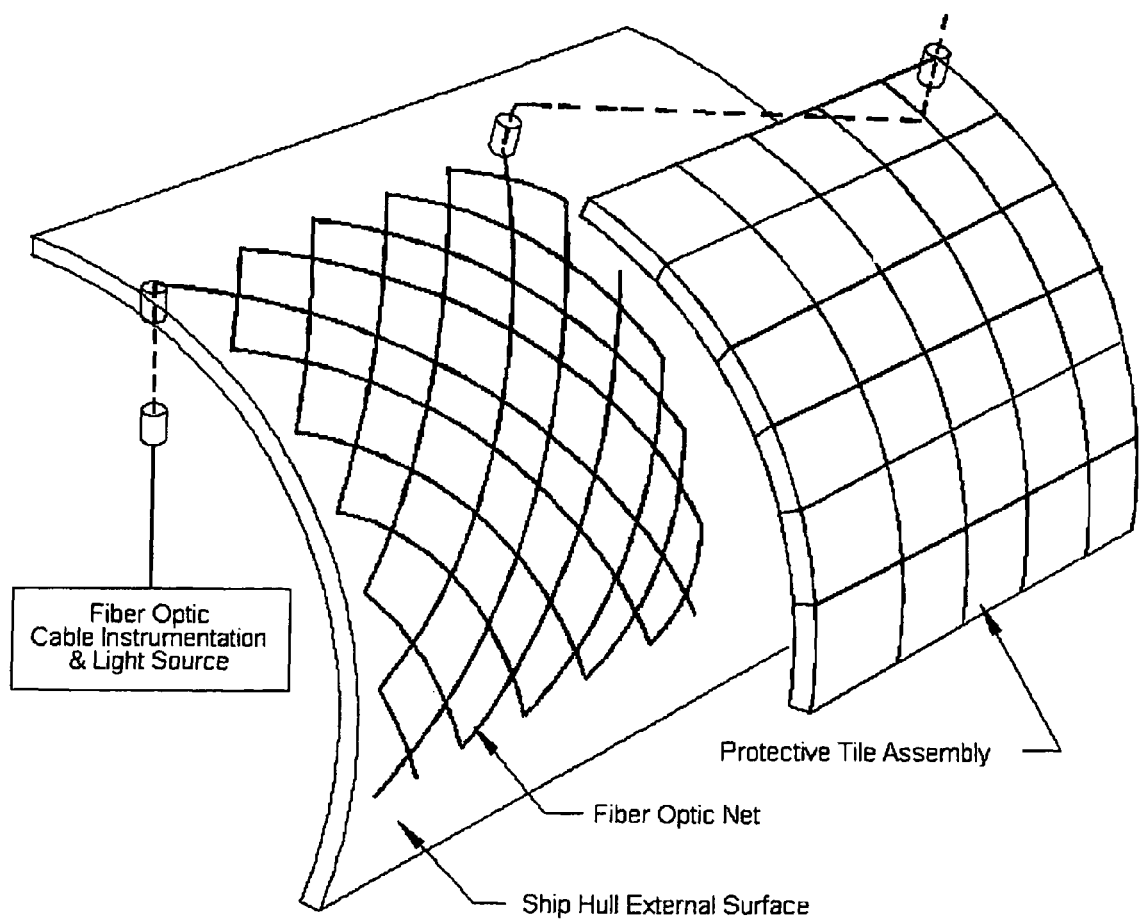
FIG. 13 is another embodiment showing an exemplary submarine hull tile bond integrity monitoring arrangement according to the present invention.
Figure 14:
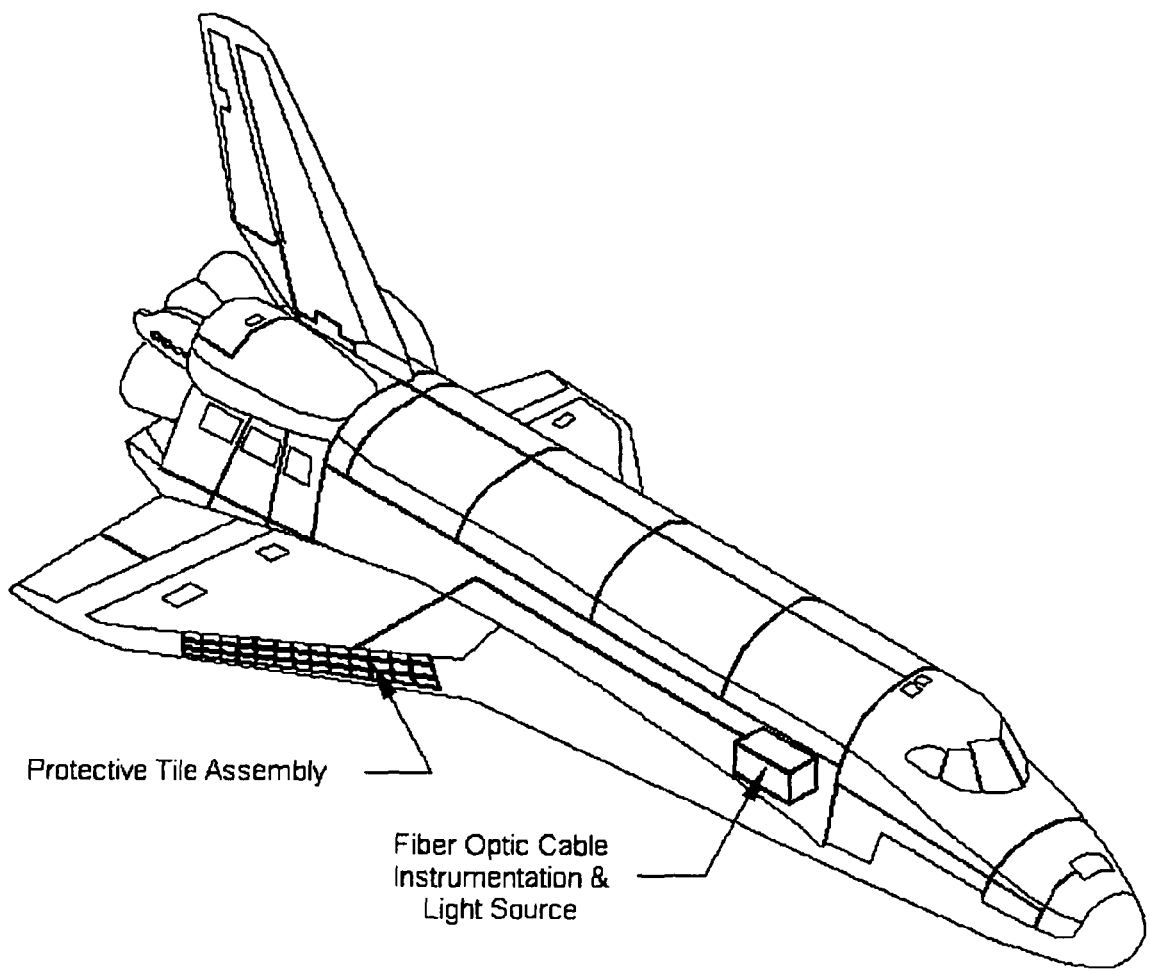
FIG. 14 is another embodiment showing an exemplary aerospace or space shuttle application whereby tile integrity can be monitored according to the present invention.

In FIGS. 13 and 14, specific applications for submarine hulls and aerospace products such a space shuttle are depicted. Methods and apparatus of the present invention can be used to provide information regarding the integrity of tiles such as those traditionally used in the space shuttle and submarines. Other similar applications where integrity of tiles or other material is of fundamental or utmost importance. In these applications, a "net" or other similar network of fiber optics are provided within the site sought to be monitored. Fiber optic cable instrumentation and a light source are then connected thereto and the fiber optic cable is adapted to provide information regarding the intergrity of the tiles or other site being monitored through the net or network of fiber optic cables. The network can be criss crossed as shown or in any other desired configuration such as irregular spaced configurations if monitoring of certain areas needs to be more specific or tailored than others. Any other configuration is also possible depending on the desired end use and application.

In the drawings and the specification, there has been set forth a preferred embodiment of the invention and, although specific terms are employed, the terms are used in a generic and descriptive sense only and not for purpose of limitation, the scope of the invention being set forth in the following claims.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

As used herein and in the following claims, articles such as "the", "a" and "an" can connote the singular or plural.

All documents referred to herein are specifically incorporated herein by reference in their entireties

What is claimed is:

1. A method of monitoring the integrity of an anti-corrosion coating of a propulsion shaft of a vessel having a hull comprising:
   a) placing an optical fiber in an anti-corrosion coating of the propulsion shaft wherein the propulsion shaft extends from a propeller through the hull and into the interior of the vessel;
   b) attaching a connector to an end of said optical fiber within the interior of the vessel;
   c) attaching sensors to said optical fiber along the propulsion shaft including a portion of the shaft extending from the propeller to the hull exterior of the vessel;
   d) connecting said connector to devices for sending signals through said optical fiber to determine the integrity of the anti-corrosion coating.

2. A propulsion shaft of a vessel comprising:
   a) a propulsion shaft core having a propeller at a first end and adapted at a second end for connection to the vessel's engine;
   b) an FRP anti-corrosion coating surrounds the propulsion shaft core and rotates with the propulsion shaft core;
   c) a plurality of sensors located within said anti-corrosion coating and encircling said propulsion shaft core;
   d) said plurality of sensors having an optical harness connected thereto;
   e) said optical harness including connectors extending from said FRP anti-corrosion coating to deliver and retrieve optical signals from said plurality of sensors and transmit said signals to a signal measurement device.

3. The propulsion shaft as set forth in claim 2, wherein;
   a) said connectors of said optical harness being disconnected from said signal measurement device when said propulsion shaft is in motion.

4. The propulsion shaft as set forth in claim 2, wherein:
   a) said FRP anti-corrosion coating includes multiple layers and a sensor is located between at least two of said multiple layers.

5. The propulsion shaft as set forth in claim 2, wherein:
   a) said at least one sensor includes a humidity sensor and a corrosion sensor.

* * * * *